United States Patent
Nara et al.

(10) Patent No.: US 9,079,931 B2
(45) Date of Patent: Jul. 14, 2015

(54) RUTHENIUM COMPLEX AND METHOD FOR PREPARING OPTICALLY ACTIVE ALCOHOL COMPOUND

(75) Inventors: Hideki Nara, Kanagawa (JP); Tohru Yokozawa, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 131 days.

(21) Appl. No.: 13/643,683

(22) PCT Filed: Dec. 14, 2010

(86) PCT No.: PCT/JP2010/072838
§ 371 (c)(1),
(2), (4) Date: Oct. 26, 2012

(87) PCT Pub. No.: WO2011/135753
PCT Pub. Date: Nov. 3, 2011

(65) Prior Publication Data
US 2013/0041151 A1 Feb. 14, 2013

Related U.S. Application Data

(60) Provisional application No. 61/331,535, filed on May 5, 2010.

(30) Foreign Application Priority Data

Apr. 28, 2010 (JP) .................. 2010-104552

(51) Int. Cl.
*C07F 15/00* (2006.01)
*B01J 31/18* (2006.01)
*B01J 31/24* (2006.01)
*C09B 57/10* (2006.01)

(52) U.S. Cl.
CPC ......... *C07F 15/0046* (2013.01); *B01J 31/1805* (2013.01); *B01J 31/2409* (2013.01); *C07F 15/0053* (2013.01); *C09B 57/10* (2013.01); *B01J 2231/643* (2013.01); *B01J 2531/0241* (2013.01); *B01J 2531/821* (2013.01)

(58) Field of Classification Search
CPC .................................................... C07F 15/0046
See application file for complete search history.

(56) References Cited

FOREIGN PATENT DOCUMENTS

| JP | 11-189600 A | 7/1999 |
|---|---|---|
| WO | 2007005550 A1 | 1/2007 |
| WO | 2009007443 A3 | 5/2009 |

OTHER PUBLICATIONS

Matsumura "Chiral Ruthenabicyclic Complexes: Precatalysts for Rapid, Enantioselective, and Wide-Scope Hydrogenation of Ketones" J. Am. Chem. Soc. 2011, 133, 10696-10699.*
Zhang "Synthesis of Chiral Bisphosphines with Tunable Bite Angles and Their Applications in Asymmetric Hydrogenation of_-Ketoesters" J. Org. Chem. 2000, 65, 6223-6226.*
International Preliminary Report on Patentability issued in corresponding International Application Ser. No. PCT/JP2010/072838, Apr. 25, 2010, 10 pages.

\* cited by examiner

*Primary Examiner* — David K O Dell
(74) *Attorney, Agent, or Firm* — Mintz Levin Cohn Ferris Glovsky and Popeo, P.C.; Peter F. Corless; Christopher R. Cowles

(57) ABSTRACT

The present invention provides a novel ruthenium complex which has an excellent catalytic activity in terms of reactivity for asymmetric reduction of a carbonyl compound and enantioselectivity, a catalyst using the ruthenium complex, and a method for preparing optically active alcohol compounds using the ruthenium complex. The present invention relates to a ruthenium complex having ruthenacycle structure, a catalyst for asymmetric reduction consisting of the ruthenium complex, and a method for preparing optically active alcohol using the ruthenium complex.

19 Claims, No Drawings

RUTHENIUM COMPLEX AND METHOD FOR PREPARING OPTICALLY ACTIVE ALCOHOL COMPOUND

CROSS-REFERENCES TO RELATED APPLICATIONS

This application is a 35 U.S.C. §371 U.S. national entry of International Application PCT/JP2010/072838 (WO 2011/135753) having an International filing date of Dec. 14, 2010, which claims under 35 U.S.C. §119(a) the benefit of Japanese Application No. 2010-104552, filed Apr. 28, 2010, and U.S. Provisional Application No. 61/331,535, filed May 5, 2010, the entire contents of which are incorporated herein by reference.

TECHNICAL FIELD

The present invention relates to a novel ruthenium complex and a method for preparing an optically active alcohol compound using the same as a catalyst.

BACKGROUND ART

A transition metal complex which has an optically active diphosphine compound as a ligand is very useful as a catalyst for an asymmetric reaction, and until now many catalysts have been developed.

Among the catalysts, in combination of a base compound, a ruthenium-diphosphine-diamine complex is known as a highly active catalyst for an asymmetric hydrogenation (for example, PLT 1). As a method for synthesizing the complex, [RuCl$_2$(p-cymene)]$_2$ as a precursor of the complex reacted with an optically active diphosphine and an optically active diamine in order in a specific solvent is known (PLT 2), as an example. In addition, as a complex having an optically active diphosphine and a tridentate amine ligand, the compound represented by the following formula is known (PLT 3).

[Chem.1]

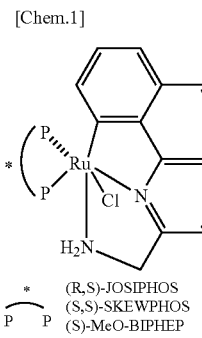

\*    (R,S)-JOSIPHOS
⌒    (S,S)-SKEWPHOS
P   P    (S)-MeO-BIPHEP

The ruthenium metal complex having an optically active diphosphine compound and a diamine compound as a ligand is highly useful because of the use for asymmetric hydrogenation of various carbonyl compounds, showing a high activity and high enantioselectivity, and giving an optically active alcohol compound with high optical purity. However, such catalyst shows high performance but not for every carbonyl compound, then development of a catalyst with higher activity is needed.

CITATION LIST

Patent Literature

PLT 1: Japanese Patent Application Laid-Open (JP-A) No. 11-189600
PLT 2: WO 2007/005550 A1
PLT 3: WO 2009/007443 A2

SUMMARY OF INVENTION

Technical Problem

The present invention provides a novel ruthenium metal complex having an excellent catalytic activity with an optically active diphosphine compound and a diamine compound as a ligand, and an asymmetric reduction catalyst using the metal complex, and a method for asymmetric reduction of a carbonyl compound using the metal complex.

Solution to Problem

Inventors of the present invention intensively studied to solve the problems described above, and as a result, found a novel ruthenium complex having an optically active diphosphine and a tridentate diamine as a ligand which was used for an asymmetric reduction, and also developed a method for obtaining an optically active alcohol with high selectivity and higher activity than the catalysts of conventional technologies by using the complex as a catalyst.

Specifically, the present invention provides a novel ruthenium complex, an asymmetric reduction catalyst which includes the metal complex, and a method for preparing optically active alcohols according to asymmetric reduction by using the metal complex.

The present invention provides the following [1] to [21].

[1] A ruthenium complex represented by the following Formula (1)

[Chem. 2]

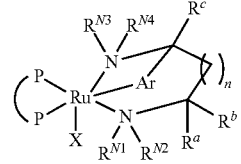

(1)

(in the formula, P⌒P represents diphosphine and X represents an anionic group; R$^a$, R$^b$ and R$^c$ each independently represent a hydrogen atom, an optionally substituted C$_1$-C$_{20}$ alkyl group, an optionally substituted C$_2$-C$_{20}$ alkenyl group, an optionally substituted C$_3$-C$_8$ cycloalkyl group, an optionally substituted C$_7$-C$_{20}$ aralkyl group, an optionally substituted aryl group, or an optionally substituted heterocyclic group, and R$^b$ and R$^c$ may form an alkylene group or an allylenedioxy group; R$^{N1}$, R$^{N2}$, R$^{N3}$, and R$^{N4}$ each independently represent a hydrogen atom, an optionally substituted C$_1$-C$_{20}$ alkyl group, an optionally substituted C$_2$-C$_{20}$ alkenyl group, an optionally substituted C$_7$-C$_{20}$ aralkyl group, or an optionally substituted C$_3$-C$_8$ cycloalkyl group, at least one of R$^{N1}$, R$^{N2}$, R$^{N3}$, and R$^{N4}$ represents a hydrogen atom, and R$^{N1}$ and R$^a$ may form an alkylene group; n represents an integer of 0 to 3; and Ar represents an optionally substituted arylene group).

[2] The ruthenium complex according to the above [1], wherein the ruthenium complex is a ruthenium complex represented by the following Formula (2)

[Chem. 3]

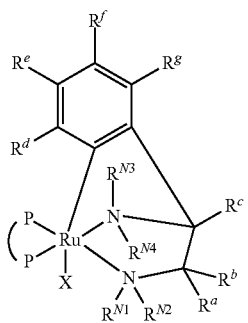
(2)

(in the formula, P⌒P represents diphosphine, X represents an anionic group; $R^a$, $R^b$, and $R^c$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloallyl group, an optionally substituted $C_7$-$C_{20}$ aralkyl group, an optionally substituted aryl group, or an optionally substituted heterocyclic group, and $R^b$ and $R^c$ may form an alkylene group or an alkylenedioxy group; $R^d$, $R^e$, $R^f$ and $R^g$ each independently represent a hydrogen atom, an alkyl group having 1 to 20 carbon atoms, a halogenated alkyl group having 1 to 5 carbon atoms, a halogen atom, an optionally substituted aryl group, an optionally substituted $C_3$-$C_8$ cycloallyl group, a tri-substituted silyl group or an alkoxy group having 1 to 20 carbon atoms; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group, or an optionally substituted $C_3$-$C_8$ cycloalkyl group, and at least one of $R^{N1}$, $R^{N2}$, $R^{N3}$ and $R^{N4}$ represents a hydrogen atom; and $R^{N1}$ and $R^a$ may form an alkylene group).

[3] The ruthenium complex according to the above [1] or [2], wherein the ruthenium complex is a ruthenium complex represented by the following Formula (3)

[Chem.4]

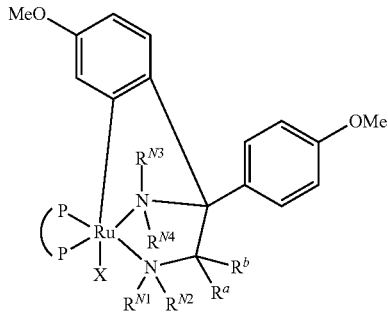
(3)

(in the formula, P⌒P represents diphosphine, X represents an anionic group, $R^a$ and $R^b$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group, or an optionally substituted heterocyclic group; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group, or an optionally substituted $C_3$-$C_8$ cycloalkyl group, and at least one of $R^{N1}$, $R^{N2}$, $R^{N3}$ and $R^{N4}$ represents a hydrogen atom; and $R^{N1}$ and $R^a$ may form an allylene group).

[4] The ruthenium complex according to any one of the above [1] to [3], wherein the diphosphine indicated as P⌒P is a diphosphine represented by the following Formula (4)

$$R^1R^2P\text{-}Q\text{-}PR^3R^4 \qquad (4)$$

(in the formula, $R^1$, $R^2$, $R^3$ and $R^4$ each independently represent an optionally substituted aryl group, an optionally substituted cycloalkyl group, or an optionally substituted alkyl group, and $R^1$ and $R^2$ and/or $R^3$ and $R^4$ may form a ring; and Q represents an optionally substituted divalent arylene group, biphenyldiyl group, binaphthalenediyl group, bipyridinediyl group, paracyclophanediyl group, or ferrocenediyl group).

[5] The ruthenium complex according to any one of the above [1] to [4], wherein the diphosphine indicated as P⌒P is an optically active diphosphine.

[6] The ruthenium complex according to any one of the above [1] to [5], wherein the optically active diphosphine indicated as P⌒P is an diphosphine represented by the following Formula (5)

[Chem.5]

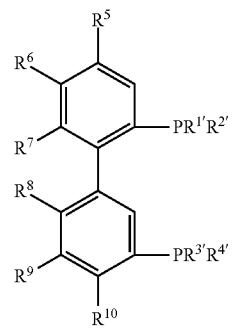
(5)

(in the formula, $R^{1'}$, $R^{2'}$, $R^{3'}$ and $R^{4'}$ each independently represent a phenyl group, a cyclopentyl group or a cyclohexyl group, and any of which is optionally substituted with a substituent group selected from a group consisting of an alkyl group having 1 to 4 carbon atoms and an alkoxy group having 1 to 4 carbon atoms. $R^5$, $R^6$, $R^7$, $R^8$, $R^9$ and $R^{10}$ each independently represent a hydrogen atom, an alkyl group having 1 to 4 carbon atoms, an alkoxy group having 1 to 4 carbon atoms, a halogen atom, a halogenated alkyl group or an dialkylamino group having 1 to 4 carbon atoms and two of $R^5$, $R^6$ and $R^7$ may form an optionally substituted alkylene group; an optionally substituted alkylenedioxy group; or an optionally substituted aromatic ring, two of $R^8$, $R^9$ and $R^{10}$ may form an optionally substituted alkylene group; an optionally substituted allylenedioxy group; or an optionally substituted aromatic ring; and $R^7$ and $R^8$ may form an optionally substituted alkylene group; an optionally substituted alkylenedioxy group; or an optionally substituted aromatic ring, with the proviso that any of $R^7$ and $R^8$ is not a hydrogen atom).

[7] The ruthenium complex according to the above [6], wherein $R^1$, $R^2$, $R^3$ and $R^4$ in the Formula (4) and $R^{1'}$, $R^{2'}$, $R^{3'}$ and $R^{4'}$ in the Formula (5) is a 3,5-xylyl group.

[8] An asymmetric reduction catalyst comprising the ruthenium complex according to any one of the above [5] to [7].

[9] A method for preparing optically active alcohols, wherein a carbonyl group is subjected to asymmetric hydrogenation with the asymmetric reduction catalyst according to the above [8] in the presence of a base compound.

[10] A method for preparing optically active alcohols, wherein a carbonyl group is subjected to asymmetric hydrogen-transfer reduction with the asymmetric reduction catalyst according to the above [8] in the presence of a base compound.

[11] A method for preparing the ruthenium complex represented by the following Formula (1),

[Chem. 6]

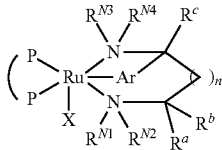

(1)

wherein the ruthenium compound represented by the following Formula (A)

[RuX(L)(P⌒P)]X  (A)

(in the formula (A), Ru represents a ruthenium atom, X represents a halogen atom, L represents an arene and P⌒P represents bisphosphine)
is reacted with the compound having the following Formula (8)

[Chem. 7]

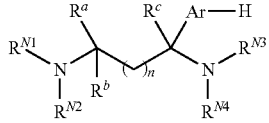

(8)

(in the formula, $R^a$, $R^b$ and $R^c$ each independently represent a hydrogen atom, an optionally substituted $C_1$-$C_{20}$ alkyl group, or an optionally substituted $C_2$-$C_{20}$ alkenyl group, or an optionally substituted $C_3$-$C_8$ cycloalkyl group, or an optionally substituted $C_7$-$C_{20}$ aralkyl group, or an optionally substituted aryl group, or an optionally substituted heterocyclic group or $R^b$ and $R^c$ may form an alkylene group or an alkylenedioxy group; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group, or an optionally substituted $C_3$-$C_8$ cycloallyl group, and at least one of $R^{N1}$, $R^{N2}$, $R^{N3}$ and $R^{N4}$ represents a hydrogen atom; or $R^{N1}$ and $R^a$ may form an alkylene group, and n is an integer of 0 to 3 and Ar represents an optionally substituted arylene group).

[12] A method for preparing the ruthenium complex represented by the following Formula (1),

[Chem. 8]

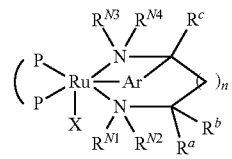

(1)

wherein the ruthenium compound represented by the following Formula (B)

[RuX$_2$(L)]$_m$  (B)

(in the formula (B), Ru represents a ruthenium atom, X represents a halogen atom, L represents an arene and m represents a natural number of 2 or more)
is reacted with a diphosphine represented as P⌒P and then with the compound having the following Formula (8)

[Chem. 9]

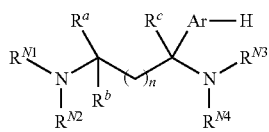

(8)

(in the formula, $R^a$, $R^b$ and $R^c$ each independently represent a hydrogen atom, an optionally substituted $C_1$-$C_{20}$ alkyl group, or an optionally substituted $C_2$-$C_{20}$ alkenyl group, or an optionally substituted $C_3$-$C_8$ cycloalkyl group, or an optionally substituted $C_7$-$C_{20}$ aralkyl group, or an optionally substituted aryl group, or an optionally substituted heterocyclic group or $R^b$ and $R^c$ may form an alkylene group or an alkylenedioxy group; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group, or an optionally substituted $C_3$-$C_8$ cycloalkyl group, and at least one of $R^{N1}$, $R^{N2}$, $R^{N3}$ and $R^{N4}$ represents a hydrogen atom; or $R^{N1}$ and $R^a$ may be alkylene group, and n is an integer of 0 to 3 and Ar represents an optionally substituted arylene group).

[13] The method for preparing the ruthenium complex according [11] or [12], wherein the reaction was carried out in presence of a solvent, and the solvent used is an alcohol solvent.

[14] The method for preparing the ruthenium complex according to any one of the above [11] to [13], additionally wherein a base is added.

[15] The method for preparing the ruthenium complex according to any one of the above [11] to [14], wherein the diphosphine indicated as P⌒P is a diphosphine represented by the following Formula (4)

$R^1R^2P$-Q-$PR^3R^4$  (4)

(in the formula, $R^1$, $R^2$, $R^3$ and $R^4$ each independently represent an optionally substituted aryl group, an optionally substituted cycloalkyl group, or an optionally substituted alkyl group, and $R^1$ and $R^2$ and/or $R^3$ and $R^4$ may form a ring; and Q represents an optionally substituted divalent arylene group, biphenyldiyl group, binaphthalenediyl group, bipyridinediyl group, paracyclophanediyl group, or ferrocenediyl group).

[16] The method for the preparing according to any one of the above [11] to [15], wherein the diphosphine indicated as P⌒P is an optically active diphosphine.

[17] The method for preparing the ruthenium complex according to any one of the above [11] to [16], wherein the optically active diphosphine indicated as P⌒P is an optically active diphosphine represented by the following Formula (5)

[Chem. 10]

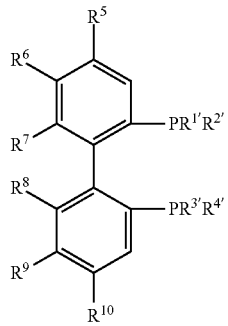

(5)

(in the formula, $R^{1'}$, $R^{2'}$, $R^{3'}$ and $R^{4'}$ each independently represent a phenyl group, a cyclopentyl group or a cyclohexyl group, and any of which is optionally substituted with a substituent group selected from a group consisting of an alkyl group having 1 to 4 carbon atoms and an alkoxy group having 1 to 4 carbon atoms. $R^5$, $R^6$, $R^7$, $R^8$, $R^9$ and $R^{10}$ each independently represent a hydrogen atom, an alkyl group having 1 to 4 carbon atoms, an alkoxy group having 1 to 4 carbon atoms, a halogen atom, a halogenated alkyl group or an dialkylamino group having 1 to 4 carbon atoms and two of $R^5$, $R^6$ and $R^7$ may form an optionally substituted alkylene group; an optionally substituted allylenedioxy group; or an optionally substituted aromatic ring, and two of $R^8$, $R^9$ and $R^{10}$ may form an optionally substituted alkylene group; an optionally substituted alkylenedioxy group; or an optionally substituted aromatic ring; and $R^7$ and $R^8$ may form an optionally substituted alkylene group; an optionally substituted alkylenedioxy group; or an optionally substituted aromatic ring, with the proviso that $R^7$ and $R^8$ are not a hydrogen atom).

[18] The method for the preparing the ruthenium complex according to any one of the above [11] to [16], wherein $R^1$, $R^2$, $R^3$ and $R^4$ in the Formula (4) and $R^{1'}$, $R^{2'}$, $R^{3'}$ and $R^{4'}$ in the Formula (5) is a 3,5-xylyl group.

[19] The method for preparing the ruthenium complex having anion group instead of halogen ion as X in the Formula (1), that the ruthenium compound having halogen ion as X in the Formula (1) reacted with other compound having anion group.

[20] The method according to [19], wherein the compounding having anion group is alkali metals carboxylate or alkali metals solfonate.

[21] The method according to [20], wherein alkali metal carboxylate is sodium acetate; alkali metal sulfonate is sodium trifluoromethanesulfonate.

Advantageous Effects of Invention

The present invention provides a novel ruthenium complex and a method for preparing an optically active alcohol compound using the complex as a catalyst. The novel ruthenium complex catalysts in the present invention shows good reactivity in asymmetric reduction of a carbonyl compound, especially conversion rate and selectivity, also shows enantioselectivity, etc., compared to conventional optically active ruthenium complex catalysts having diphosphine and diamine ligand, and therefore it is industrially highly useful.

Moreover, as the ruthenium complex is expensive, it is preferable to minimize the amount of the ruthenium complex used for reaction. In this regard, according to the invention, a complex having high catalytic activity which requires less amount of a catalyst for reaction than conventional asymmetric reduction complex is provided.

DESCRIPTION OF EMBODIMENTS

Hereinafter, the present invention will be explained in detail.

The ruthenium complex represented by the Formula (1) of the invention is characterized in that a divalent arylene group represented by —Ar— is included therein, and it is specifically characterized in that one end of the arylene group binds to the ruthenium atom with Ru-carbon bond and the other end binds to the carbon atom in the carbon chain of a diamine compound as a ligand with a carbon-carbon bond. It is further characterized in that any of the two nitrogen atoms in the diamine compound as a ligand has $sp^3$ hybridization. Moreover, the arylene group may have a substituent group such as an alkoxy group.

One of the characteristics of the ruthenium complex of the invention is that it is a ruthenium complex having ruthenacycle structure.

Examples of the optionally substituted arylene group which is represented by Ar in the ruthenium complex of the Formula (1) of the invention include a divalent monocyclic, polycyclic or condensed-ring type arylene group having 6 to 36 carbon atoms, preferably 6 to 18 carbon atoms, and more preferably 6 to 12 carbon atoms, or a divalent monocyclic, polycyclic or condensed-ring type heteroarylene group having a 3- to 8-membered, and preferably 5- to 8-membered ring in which 1 to 4, preferably 1 to 3 or 1 or 2 heteroatoms consisting of a nitrogen atom, an oxygen atom and a sulfur atom is included. Examples of a preferred arylene group include a phenylene group, a naphthalenediyl group, a pyridinediyl group, a thiophenediyl group and a furandiyl group, and a phenylene group is particularly preferable. Although the position to which the divalent arylene group binds is not specifically limited, two adjacent carbon atom positions (i.e., ortho position) are preferable.

In addition, examples of a substitutent group which is substituted on the arylene group include a linear or branched alkyl group, a linear or branched alkoxy group, a cycloalkyl group, a halogen atom, an aryl group, a heteroaryl group, and a tri-substituted silyl group.

Hereinafter, the substituent group which is substituted on the arylene group will be explained.

Examples of the linear or branched alkyl group, may be substituted by halogen atom such as F, include a linear or branched alkyl group having 1 to 10 carbon atoms, preferably 1 to 6 carbon atoms, and more preferably 1 to 4 carbon atoms. Specific examples include a methyl group, an ethyl group, a n-propyl group, an isopropyl group, a n-butyl group, an isobutyl group, a s-butyl group, a t-butyl group and a trifluoromethyl group.

Examples of the linear or branched alkoxy group include a linear or branched alkoxy group having 1 to 10 carbon atoms, preferably 1 to 6 carbon atoms, and more preferably 1 to 4 carbon atoms. Specific examples include a methoxy group, an ethoxy group, a n-propoxy group, an isopropoxy group, a n-butoxy group, a s-butoxy group, an isobutoxy group and a t-butoxy group.

Examples of the cycloalkyl group include a saturated or unsaturated monocyclic, polycyclic or condensed-ring type cycloalkyl group having 3 to 15 carbon atoms, and preferably 5 to 7 carbon atoms, and specific examples include a cyclopentyl group and a cyclohexyl group. One or two or more alkyl groups having 1 to 4 carbon atoms or alkoxy groups having 1 to 4 carbon atoms may be substituted on the ring of these cycloalkyl groups.

Examples of the halogen atom include a chlorine atom, a bromine atom and a fluorine atom.

Examples of the aryl group include an aryl group having 6 to 14 carbon atoms, and specific examples include a phenyl group, a naphthyl group, an anthryl group, a phenanthryl group and a biphenyl group. The aryl group may have one or two or more substituent groups, and examples of the substituent group include an alkyl group having 1 to 4 carbon atoms and an alkoxy group having 1 to 4 carbon atoms as described above.

Examples of the heteroaryl group include a 5-membered or 6-membered cyclic group having an oxygen atom, a sulfur atom or a nitrogen atom, and specific examples include a furyl group, a thienyl group and a pyridyl group.

Examples of the tri-substituted silyl group include a silyl group which is tri-substituted with the alkyl group or the aryl group described above, and specific examples include a trimethylsilyl group, a triethylsilyl group, a triisopropylsilyl group, a tert-butyldimethylsilyl group, a diphenylmethylsilyl group and a dimethylphenylsilyl group.

Examples of the anionic group represented by X in the ruthenium complex of the Formulae (1), (2) and (3) include a hydride ion ($H^-$); a halogen ion such as a chloride ion ($Cl^-$), a bromide ion ($Br^-$), or an iodide ion ($I^-$) and a complex anion such as $BH_4$, $BF_4$, $BPh_4$, $PF_6$, an acetoxy group (OAc) and a trifluoromethane sulfonyloxy group (OTf). Among these, a halogen ion is preferable.

The groups represented by $R^a$, $R^b$, $R^c$, $R^d$, $R^e$, $R^f$, $R^g$, $R^{N1}$, $R^{N2}$, $R^{N3}$ and $R^{N4}$ in the ruthenium complex of the Formulae (1), (2) and (3) will be explained hereinafter.

Examples of the $C_1$-$C_{20}$ alkyl group include a linear or branched alkyl group having 1 to 20 carbon atoms, preferably 1 to 5 carbon atoms and more preferably 1 to 4 carbon atoms, and specific examples include a methyl group, an ethyl group, a n-propyl group, an isopropyl group, a n-butyl group, an isobutyl group, a sec-butyl group, a t-butyl group, a n-pentyl group, a n-hexyl group, a decyl group, a dodecyl group, and a hexadecyl group.

Examples of the $C_2$-$C_{20}$ alkenyl group include a liner or branched alkenyl group having 2 to 20 carbon atoms, preferably 2 to 10 carbon atoms and more preferably 2 to 6 carbon atoms, and specific examples include an ethenyl group, a n-propenyl group, an isopropenyl group, a 1-butenyl group, a 1-buten-2-yl group, a pentenyl group, and a hexenyl group.

Examples of the $C_1$-$C_{20}$ alkoxy group include an alkyl group having 1 to 20 carbon atoms to which an oxygen atom is bonded, and specific examples include a methoxy group, an ethoxy group, a n-propoxy group, an isopropoxy group, a n-butoxy group, a s-butoxy group, an isobutoxy group and a t-butoxy group.

The examples of halogenated $C_1$-$C_5$ alkyl group, include trifluoromethyl group, pentafluoroethyl group, heptafluoropropyl group, trichoromethyl group.

Examples of the $C_3$-$C_8$ cycloalkyl group include a saturated or unsaturated monocyclic, polycyclic or condensed-ring type cycloalkyl group having 3 to 8 carbon atoms, and preferably 5 to 7 carbon atoms. Specific examples include a cyclopentyl group and a cyclohexyl group.

Examples of the halogen atom include a chlorine atom, a bromine atom and a fluorine atom.

Examples of the heteroaryl group include a 5-membered or 6-membered cyclic group having an oxygen atom, a sulfur atom or a nitrogen atom, and specific examples include a furyl group, a thienyl group and a pyridyl group.

Examples of the tri-substituted silyl group include a silyl group which is tri-substituted with the alkyl group or the aryl group described above, and specific examples include a trimethylsilyl group, a triethylsilyl group, a triisopropylsilyl group, a tert-butyldimethylsilyl group, a diphenylmethylsilyl group and a dimethylphenylsilyl group.

Examples of the $C_7$-$C_{20}$ aralkyl group include an aralkyl group having 7 to 20 carbon atoms, preferably 7 to 15 carbon atoms and more preferably 7 to 10 carbon atoms in which an alkyl group having 1 to 20 carbon atoms is bonded to a monocyclic, polycyclic or condensed-ring type aryl group having 6 to 19 carbon atoms and preferably 6 to 14 carbon atoms. Specific examples include a benzyl group, a α-methylbenzyl group, a α,α-dimethylbenzyl group, a 2-phenylethyl group and a 3-phenylpropyl group.

Otherwise, the examples of the substituent to $C_1$-$C_{20}$ alkyl group, $C_2$-$C_{20}$ alkenyl group, $C_1$-$C_{20}$ alkoxy group, halogenated $C_1$-$C_5$ alkyl group, $C_3$-$C_8$ cycloalkyl group, heteroaryl group, tri-substituted silyl group, and $C_7$-$C_{20}$ aralkyl group as described above include linear or branched alkyl group, linear or branched alkoxy group, cycloalkyl group, halogen atom, aryl group, heteroaryl group, and tri-substituted silyl group.

Examples of an aryl group in the optionally substituted aryl group include a monocyclic, polycyclic or condensed-ring type aryl group having 6 to 20 carbon atoms, preferably 6 to 14 carbon atoms, and more preferably 6 to 12 carbon atoms. Specific examples include a phenyl group, a naphthyl group, an anthryl group, a phenanthryl group and a biphenyl group, and a phenyl group is preferable. The aryl group may have one or two or more substituent groups and examples of the substituent group include an alkyl group having 1 to 4 carbon atoms such as a methyl group, an isopropyl group and a t-butyl group, and; an alkoxy group having 1 to 4 carbon atoms such as a methoxy group, an ethoxy group, a n-propoxy group, an isopropoxy group, a n-butoxy group, an isobutoxy group, a s-butoxy group and a t-butoxy group as described above.

The examples of an optionally substituted heterocyclic group include a 5-membered or 6-membered cyclic group having an oxygen atom, a sulfur atom or a nitrogen atom, and specific examples include a furyl group, a thienyl group and a pyridyl group. And the examples of the substituent which the heterocyclic group has one or more than two of include alkyl group having 1 to 4 carbon atoms such as a methyl group, an isopropyl group, and a t-butyl group; alkoxy group having 1 to 4 carbon atoms such as a methoxy group, an ethoxy group, a n-propoxy group, an isopropoxy group, a n-butoxy group, a s-butoxy group, an isobutoxy group and a t-butoxy group.

Moreover, examples of the alkylene group formed by $R^b$ and $R^c$ include a linear or branched alkylene group having 1 to 6 carbon atoms and preferably 1 to 4 carbon atoms. Specific examples include a methylene group, an ethylene group, a trimethylene group, a propylene group and a tetramethylene group, and these alkylene groups are optionally substituted with an alkyl group having 1 to 4 carbon atoms or an alkoxy group having 1 to 4 carbon atoms.

Examples of the alkylenedioxy group formed by $R^b$ and $R^c$ include a linear or branched alkylenedioxy group having 1 to 6 carbon atoms and preferably 1 to 4 carbon atoms. Specific examples include a methylenedioxy group, an ethylenedioxy group, and a trimethylenedioxy group.

The examples of the alkylene group formed by $R^{N1}$ and $R^a$ include a linear or branched alkylene group having 1 to 6 carbon atoms and preferably 1 to 4 carbon atoms. Specific examples include a methylene group, an ethylene group, a trimethylene group, a propylene group and a tetramethylene group, and these alkylene groups are optionally substituted with an alkyl group having 1 to 4 carbon atoms or an alkoxy group having 1 to 4 carbon atoms.

The diphosphine (also as named bisphosphine) represented by P⌒P in the ruthenium complex of the Formulae (1), (2) and (3) is not specifically limited if it is a diphosphine which can coordinate to ruthenium. Examples thereof include those represented by the following Formula (4)

$$R^1R^2P\text{-}Q\text{-}PR^3R^4 \quad (4)$$

(in the formula, $R^1$, $R^2$, $R^3$ and $R^4$ each independently represent an optionally substituted aryl group, an optionally substituted cycloalkyl group, or an optionally substituted alkyl group, and $R^1$ and $R^2$ and/or $R^3$ and $R^4$ may form a ring. Q represents an optionally substituted divalent arylene group, biphenyldiyl group, binaphthalenediyl group, bipyridinediyl group, paracyclophanediyl group, or ferrocenediyl group).

Examples of the optionally substituted aryl group represented by $R^1$, $R^2$, $R^3$ and $R^4$ in the above formula include an aryl group having 6 to 14 carbon atoms, and specific examples include a phenyl group, a naphthyl group, an anthryl group, a phenanthryl group and a biphenyl group.

These aryl groups may have one or two or more substituent groups and the examples of the substituent group include an alkyl group and an alkoxy group.

Examples of the alkyl group as a substituent group for the aryl group include a linear or branched alkyl group having 1 to 15 carbon atoms, preferably 1 to 10 carbon atoms and more preferably 1 to 6 carbon atoms, and specific examples include a methyl group, an ethyl group, a n-propyl group, an isopropyl group, a n-butyl group, a s-butyl group, an isobutyl group and a t-butyl group.

Examples of the alkoxy group as a substituent group for the aryl group include a linear or branched alkoxy group having 1 to 6 carbon atoms, and specific examples include a methoxy group, an ethoxy group, a n-propoxy group, an isopropoxy group, a n-butoxy group, a s-butoxy group, an isobutoxy group and a t-butoxy group.

Moreover, examples of the optionally substituted cycloalkyl group represented by $R^1$, $R^2$, $R^3$ and $R^4$ include a 5-membered or 6-membered cycloalkyl group, and preferred examples of the cycloalkyl group include a cyclopentyl group and a cyclohexyl group. On the ring of these cycloalkyl groups, one or two or more substituent groups such as an alkyl group or an alkoxy group, which is mentioned above as a substituent group for the aryl group, may be substituted.

Examples of the optionally substituted alkyl grow include a linear or branched alkyl group having 1 to 15 carbon atoms, preferably 1 to 10 carbon atoms and more preferably 1 to 6 carbon atoms, and specific examples include a methyl group, an ethyl group, a n-propyl group, an isopropyl group, a n-butyl group, a s-butyl group, an isobutyl group and a t-butyl group. These alkyl groups are optionally substituted with one or two or more substituent groups such as alkoxy group which is mentioned as a substituent group for the aryl group in the above.

Moreover, examples of the ring which may be formed by $R^1$ and $R^2$ and/or $R^3$ and $R^4$ include a ring which includes a phosphorus atom to which $R^1$, $R^2$, $R^3$ and $R^4$ are bonded, including a 4-membered, a 5-membered or a 6-membered ring. Specific examples include a phosphetane ring, a phospholane ring, a phosphane ring, 2,4-dimethyl phosphetane ring, 2,4-diethyl phosphetane ring, 2,5-dimethyl phospholane ring, 2,5-diethyl phospholane ring, 2,6-dimethyl phosphane ring and 2,6-diethyl phosphane ring, and these ring compounds may be optically active.

Moreover, examples of Q include an optionally substituted divalent arylene group, biphenyldiyl group, binaphthalenediyl group, bipyridinediyl group, paracyclophanediyl group, and a ferrocenediyl group.

Examples of the divalent arylene group include a divalent arylene group which is derived from the aryl group described above. Preferred examples of the arylene group include a phenylene group. Examples of the phenylene group include an o- or m-phenylene group, and the phenylene group is optionally substituted with an alkyl group having 1 to 6 carbon atoms such as a methyl group, an ethyl group, a n-propyl group, an isopropyl group, a n-butyl group, a s-butyl group, an isobutyl group and a t-butyl group; an alkoxy group having 1 to 6 carbon atoms such as a methoxy group, an ethoxy group, a n-propoxy group, an isopropoxy group, a n-butoxy group, a s-butoxy group, an isobutoxy group and a t-butoxy group; a hydroxy group; an amino group, or, a substituted amino group.

The biphenyldiyl group, binaphthalenediyl group and bipyridinediyl group preferably have a 1,1'-biaryl-2,2'-diyl type structure in which an axial asymmetric structure is included, and the biphenyldiyl group, binaphthalenediyl group and bipyridinediyl group are optionally substituted with the alkyl group and alkoxy group described above, for example, an alkylenedioxy group such as a methylenedioxy group, an ethylenedioxy group and a trimethylenedioxy group, a hydroxy group, an amino group, and a substituted amino group.

Paracyclophanediyl group may be optionally substituted with the alkyl group and alkoxy group described above, for example, an alkylenedioxy group such as a methylenedioxy group, an ethylenedioxy group and a trimethylenedioxy group, a hydroxy group, an amino group, and a substituted amino group.

Moreover, the ferrocenediyl group is also optionally substituted and examples of the substituent group include an alkyl group, an alkoxy group, an alkylenedioxy group, a hydroxy group, an amino group, and a substituted amino group as described above.

Examples of the substituted amino group include an amino group which is substituted with one or two alkyl groups having 1 to 6 carbon atoms.

Specific examples of the diphosphine represented by the Formula (4) include optically active diphosphines that are well known in the art, and preferred examples include the compound represented by the following Formula (5).

The optically active disphosphine represented by the following formula can be mentioned.

[Chem. 11]

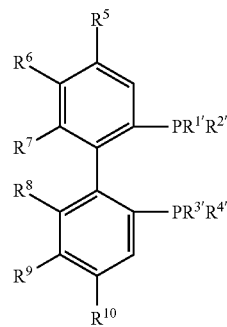

(5)

(in the formula, $R^{1'}$, $R^{2'}$, $R^{3'}$ and $R^{4'}$ each independently represent a phenyl group, a cyclopentyl group or a cyclohexyl group, and any of which is optionally substituted with a substituent group selected from a group consisting of an alkyl group having 1 to 4 carbon atoms and an alkoxy group having 1 to 4 carbon atoms. $R^5$, $R^6$, $R^7$, $R^8$, $R^9$ and $R^{10}$ each independently represent a hydrogen atom, an alkyl group having 1 to 4 carbon atoms, an alkoxy group having 1 to 4 carbon atoms, a halogen atom, a halogenated alkyl group or an dialkylamino group having 1 to 4 carbon atoms, two of $R^5$, $R^6$ and $R^7$ may form an optionally substituted alkylene group; an optionally substituted alkylenedioxy group; or an optionally substituted aromatic ring, and two of $R^8$, $R^9$ and $R^{10}$ may form an optionally substituted alkylene group; an optionally substituted alkylenedioxy group; or an optionally substituted aromatic ring. Furthermore, $R^7$ and $R^8$ may form an optionally substituted alkylene group; an optionally substituted alkylenedioxy group; or an optionally substituted aromatic ring, with the proviso that $R^7$ and $R^8$ are not a hydrogen atom.)

Regarding the alkyl group, alkoxy group, halogen, alkylene group, and alkylenedioxy group in the above Formula (5), those described in the above can be mentioned. The aromatic ring which is formed by two groups may form a 6-membered aromatic ring together with adjacent atom. The aromatic ring thus formed is optionally substituted with an alkyl group or an alkoxy group.

Preferred examples of the Formula (5) include cases in which $R^{1'}$, $R^{2'}$, $R^{3'}$ and $R^{4'}$ each independently represent a phenyl group which is optionally substituted singular or plural number with a substituent group selected from a group consisting of an alkyl group having 1 to 4 carbon atoms and an alkoxy group having 1 to 4 carbon atoms; and $R^6$ and $R^7$ forms a tetramethylene group; a methylenedioxy group which is optionally substituted with an alkyl group having 1 to 4 carbon atoms or a fluorine atom; or forms a benzene ring together with an adjacent carbon atom; and $R^8$ and $R^9$ forms a tetramethylene group; a methylenedioxy group which is optionally substituted with an alkyl group having 1 to 4 carbon atoms or a fluorine atom; or forms a benzene ring together with an adjacent carbon atom.

Moreover, specific examples of more preferable optically active diphosphine of the invention include the optically active diphosphine represented by the following Formula (6) or Formula (7).

[Chem. 12]

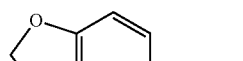

(6)

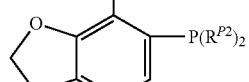

(7)

Specific examples of $R^{P1}$ and $R^{P2}$ in the Formula (6) and the specific examples of $R^{P3}$ and $R^{P4}$ in the Formula (7) include a phenyl group, a p-tolyl group, a m-tolyl group, an o-tolyl group, a 3,5-xylyl group, a 3,5-di-t-butylphenyl group, a p-t-butylphenyl group, a p-methoxyphenyl group, a 3,5-di-t-butyl-4-methoxyphenyl group, a p-chlorophenyl group, a m-chlorophenyl group, a p-fluorophenyl group and a m-fluorophenyl group.

Specific examples of the diphosphine represented by the Formula (4), (5), (6) and (7) of the invention include 2,2'-bis(diphenylphosphino)-1,1'-binaphthyl(binap); 2,2'-bis[di(p-tolyl)phosphino]-1,1'-binaphthyl(tolbinap); 2,2'-bis[di(m-tolyl)phosphino]-1,1'-binaphthyl; 2,2'-bis[di(3,5-xylyl)phosphino]-1,1'-binaphthyl(xylbinap); 2,2'-bis[di(p-t-butylphenyl)phosphino]-1,1'-binaphthyl; 2,2'-bis[di(p-methoxyphenyl)phosphino]-1,1'-binaphthyl; 2,2'-bis[di(3,5-di-t-butyl-4-methoxyphenyl)phosphino]-1,1'-binaphthyl; 2,2'-bis[di(cyclopentyl)phosphino]-1,1'-binaphthyl; 2,2'-bis[di(cyclohexyl)phosphino]-1,1'-binaphthyl; 2,2'-bis(diphenylphosphino)-5,5',6,6',7,7',8,8'-octahydro-1,1'-binaphthyl; 2,2'-bis(di-p-tolylphosphino)-5,5',6,6',7,7',8,8'-octshydro-1,1'-binaphthyl; 2,2'-bis(di-m-tolylphosphino)-5,5',6,6',7,7',8,8'-octahydro-1,1'-binaphthyl; 2,2'-bis(di-3,5-xylylphosphino)-5,5',6,6',7,7',8,8'-octahydro-1,1'-binaphthyl(xylyl-H8-binap); 2,2'-bis(di-p-t-butylphenylphosphino)-5,5',6,6',7,7',8,8'-octahydro-1,1'-binaphthyl; 2,2'-bis(di-p-methoxyphenylphosphino)-5,5',6,6',7,7',8,8'-octahydro-1,1'-binaphthyl; 2,2'-bis(di-p-chlorophenylphosphino)-5,5',6,6',7,7',8,8'-octahydro-1,1'-binaphthyl; 2,2'-bis(dicyclopentylphosphino)-5,5',6,6',7,7',8,8'-octahydro-1,1'-binaphthyl; 2,2'-bis(dicyclohexylphosphino)-5,5',6,6',7,7',8,8'-octahydro-1,1'-binaphthyl; ((4,4'-bi-1,3-benzodioxol)-5,5'-diyl)bis(diphenylphosphine)(segphos); (4,4'-bi-1,3-benzodioxol)-5,5'-diyl)bis(di(3,5-xylyl)phosphine) (dm-segphos); ((4,4'-bi-1,3-benzodioxol)-5,5'-diyl)bis(di(3,5-di-t-butyl-4-methoxyphenyl)phosphine); ((4,4'-bi-1,3-benzodioxol)-5,5'-diyl)bis(di(4-methoxyphenyl)phosphine); ((4,4'-bi-1,3-benzodioxol)-5,5'-diyl)bis(dicyclohexylphosphine); ((4,4'-bi-1,3-benzodioxol)-5,5'-diyl)bis(bis(3,5-di-t-butylphenyl)phosphine); 2,2'-bis(di-3,5-xylylphosphino)-6,6'-dimethoxy-1,1'-biphenyl(xylyl-MeO-biphep); 2,2'-bis(diphenylphosphino)-6,6'-dimethyl-1,1-biphenyl; 2,2'-bis(cli-p-tolylphosphino)-6,6'-dimethyl-1,1'-biphenyl; 2,2'-bis(di-o-tolylphosphino)-6,6'-dimethyl-1,1'-biphenyl; 2,2'-bis(di-m-fluorophenylphosphino)-6,6'-dimethyl-1,1'-biphenyl; 2,2'-bis(diphenylphosphino)-6,6'-dimethoxy-1,1'-biphenyl; 2,2'-bis(di-p-tolylphosphino)-6,6'-dimethoxy-1,1'-biphenyl; 2,2',6,6'-tetramethoxy-4,4'-bis(di-3,5-xylylphosphino)-3,3'-bipyridine (xylyl-p-phos); 2,2',6,6'-tetramethoxy-4,4'-bis(diphenylphosphino)-3,3'-bipyridine; 2,2',6,6'-tetramethoxy-4,4'-bis(di-p-tolylphosphino)-3,3'-bipyridine; 2,2',6,6'-tetramethoxy-4,4'-bis(di-o-tolylphosphino)-3,3'-bipyridine; 4,12-bis(di-3,5-xylylphosphino)-[2.2]-paracyclophane; 4,12-bis(diphenylphosphino)-[2.2]-paracyclophane; 4,12-bis(di-p-tolylphosphino)-[2.2]-paracyclophane; 4,12-bis(di-o-tolylphosphino)-[2.2]-paracyclophane; 1,1'-bis(2,4-diethylphosphotano)ferrocene; 1,13-bis(diphenylphosphino)-7,8-dihydro-6H-dibenzo[f,h][1,5]dioxonin; 1,13-bis(bis(3,5-dimethylphenyl)phosphino)-7,8-dihydro-6H-dibenzo[f,h][1,5]dioxonin (xylyl-C3-tunephos); and 6,6'-bis(bis(3,5-dimethylphenyl)phosphino)-2,2',3,3'-tetrahydro-5,5'-bi-1,4-benzodioxin(xylyl-synphos).

In addition to those described above, examples of the bisphosphine compound which can be used for the invention include N,N-dimethyl-1-[1',2-bis(diphenylphosphino)ferrocenyl]ethylamine; 2,3-bis(diphenylphosphino)butane; 1-cyclohexyl-1,2-bis(diphenylphosphino)ethane; 2,3-O-isopropylidene-2,3-dihydroxy-1,4-bis(diphenylphosphino)butane; 1,2-bis[(o-methoxyphenyl)phenylphosphino]ethane; 1,2-bis (2,5-dimethylphosphorano)ethane; N,N'-bis(diphenylphosphino)-N,N'-bis(1-phenylethyl)ethylenediamine; 1,2-bis (diphenylphosphino)propane; 2,4-bis(diphenylphosphino) pentane; cyclohexylanisylmethylphosphine; 2,3-bis (diphenylphosphino)-5-norbornene; 3,4-bis (diphenylphosphino)-1-benzylpyrrolidine; 1-[1',2-bis (diphenylphosphino)ferrocenyl]ethyl alcohol; 2,2'-bis (diphenylphosphino)-1,1'-dicyclopentane, sodium; 2,2'-bis (diphenylphosphino)-1,1'-binaphthyl-5,5'-disulfonate, sodium; 2,2'-bis(di(3,5-xylyl)phosphino)-1,1'-binaphthyl-5, 5'-disulfonate; 1,1-(2,2'-bis(diphenylphosphino)-1,1'-binaphthyl-6,6'-diyl)bis(methylene)guanidine; 1,1-(2,2'-bis(di (3,5-xylyl)phosphino)-1,1'-binaphthyl-6,6'-diyl)bis (methylene)guanidine; (6,6'-bis(tris(3,3,4,4,5,5,6,6,7,7,8,8, 8-tridecafluorooctyl)silyl)-1,1'-binaphthyl-2,2'-diyl)bis (diphenylphosphine); (6,6'-bis(tris(3,3,4,4,5,5,6,6,7,7,8,8,8-tridecafluorooctyl)silyl)-1,1'-binaphthyl-2,2'-diyl)bis(di(3, 5-xylyl)phosphine); (2,2'-bis(diphenylphosphino)-1,1'-binaphthyl-4,4'-diyl)dimethanamine.hydrogen bromide salt; (2,2'-bis(di(3,5-xylyl)phosphino)-1,1'-binaphthyl-4,4'-diyl) dimethanamine.hydrogen bromide salt; (4,4'-bis(trimethylsilyl)-1,1'-binaphthyl-2,2'-diyl)bis(diphenylphosphine); (4,4'-bis(trimethylsilyl)-1,1'-binaphthyl-2,2'-diyl)bis(di(3,5-xylyl)phosphine); (4,4'-bis(triisopropylsilyl)-1,1'-binaphthyl-2,2'-diyl)bis(diphenylphosphine); (4,4'-bis (triisopropylsilyl)-1,1'-binaphthyl-2,2'-diyl)bis(di(3,5-xylyl) phosphine); 2,2'-bis(diphenylphosphino)-1,1'-binaphthyl-4, 4'-diyldiphosphonic acid; 2,2'-bis(di(3,5-xylyl)phosphino)-1,1'-binaphthyl-4,4'-diyldiphosphonic acid; Tetraethyl 2,2'-bis(diphenylphosphino)-1,1'-binaphthyl-4,4'-diyldiphosphonate; tetraethyl 2,2'-bis(di(3,5-xylyl) phosphino)-1,1'-binaphthyl-4,4'-diyldiphosphonate; (4,4'-diphenyl-1,1'-binaphthyl-2,2'-diyl)bis(diphenylphosphine); (4,4'-diphenyl-1,1'-binaphthyl-2,2'-diyl)bis(di(3,5-xylyl) phosphine); (4,4'-dichloro-1,1'-binaphthyl-2,2'-diyl)bis (diphenylphosphine); (4,4'-dichloro-1,1'-binaphthyl-2,2'-diyl)bis(di(3,5-xylyl)phosphine); (4,4'-dibromo-1,1'-binaphthyl-2,2'-diyl)bis(diphenylphosphine); (4,4'-dibromo-1,1'-binaphthyl-2,2'-diyl)bis(di(3,5-xylyl)phosphine); (4,4'-dimethyl-1,1'-binaphthyl-2,2'-diyl)bis(diphenylphosphine); (4,4'-dimethyl-1,1'-binaphthyl-2,2'-diyl)bis(di(3,5-xylyl) phosphine); (2,2'-bis(diphenylphosphino)-1,1'-binaphthyl-4, 4'-diyl)bis(diphenylmethanol); (2,2'-bis(di(3,5-xylyl)phosphino)-1,1'-binaphthyl-4,4'-diyl)bis(diphenylmethanol); (4,4'-bis(1,1,1,2,2,3,3,4,4,5,5,6,6,8,8,9,9,10,10,11,11,12,12, 13,13,13-hexacosafluoro-7-(perfluorohexyl)tridecan-7-yl)-1,1'-binaphthyl-2,2'-diyl)bis(diphenylphosphine); (4,4'-bis (1,1,1,2,2,3,3,4,4,5,5,6,6,8,8,9,9,10,10,11,11,12,12,13,13, 13-hexacosafluoro-7-(perfluorohexyl)tridecan-7-yl)-1,1'-binaphthyl-2,2'-diyl)bis(di(3,5-xylyl)phosphine); (7,7'-dimethoxy-1,1'-binaphthyl-2,2'-diyl)bis (diphenylphosphine); (7,7'-dimethoxy-1,1'-binaphthyl-2,2'-diyl)bis(di(3,5-xylyl)phosphine); 4,4'-di-tert-butyl-4,4',5,5'-tetrahydro-3H,3'H-3,3'-bidinaphtho[2,1-c:1',2'-e] phosphapine; 1,2-bis(3H-dinaphtho[2,1-c:1',2'-e] phosphapin-4(5H)-yl)benzene, 3,3'-bis (diphenylphosphino)-4,4'-biphenanthrene; 3,3'-bis(di(3,5-xylyl)phosphino)-4,4'-biphenanthrene; (3,3'-diphenyl-1,1'-binaphthyl-2,2'-diyl)bis(methylene)bis(diphenylphosphine); (3,3'-diphenyl-1,1'-binaphthyl-2,2'-diyl)bis(methylene)bis (di(3,5-xylyl)phosphine); 2,2'-bis(diphenylphosphinooxy)-1,1'-binaphthyl; 2,2'-bis(di(3,5-xylyl)phosphinooxy)-1,1'-binaphthyl; (3,3'-dimethyl-1,1'-binaphthyl-2,2'-diyl)bis (oxy)bis(diphenylphosphine); (3,3'-dimethyl-1,1'-binaphthyl-2,2'-diyl)bis(oxy)bis(di(3,5-xylyl)phosphine); (3,3'-diphenyl-1,1'-binaphthyl-2,2'-diyl)bis(oxy)bis(diphenylphosphine); (3,3'-diphenyl-1,1'-binaphthyl-2,2'-diyl)bis (oxy)bis(di(3,5-xylyl)phosphine); (3,3'-bis(3,5-dimethylphenyl)-1,1'-binaphthyl-2,2'-diyl)bis(oxy)bis (diphenylphosphine); (3,3'-bis(3,5-dimethylphenyl)-1,1'-binaphthyl-2,2'-diyl)bis(oxy)bis(di(3,5-xylyl)phosphine); (3,3'-diphenyl-1,1'-binaphthyl-2,2'-diyl)bis(oxy)bis(bis(3,5-dimethylphenyl)phosphine); N2,N2'-bis(diphenylphosphino)-1,1'-binaphthyl-2,2'-diamine; N2,N2'-bis(di(3,5-xylyl)phosphino)-1,1'-binaphthyl-2,2'-diamine; (SP)-1-[(S)-α-(dimethylamino)-2-(diphenylphosphino)benzyl]-2-diphenylphosphinoferrocene; (RP)-1-[(R)-α-(dimethylamino)-2-(diphenylphosphino)benzyl]-2-diphenylphosphinoferrocene; (R)-1-{(RP)-2-[2-(diphenylphosphino)phenyl] ferrocenyl}ethyldiphenylphosphine; (S)-1-{(SP)-2-[2-(diphenylphosphino)phenyl] ferrocenyl}ethyldiphenylphosphine; (R)-1-{(RP)-2-[2-(diphenylphosphino)phenyl] ferrocenyl}ethyldicyclophosphine; (S)-1-{(SP)-2-[2-(diphenylphosphino)phenyl] ferrocenyl}ethyldicyclophosphine; (R)-1-{(RP)-2-[2-(diphenylphosphino)phenyl]ferrocenyl}ethyl di(2-norbonyl) phosphine; (S)-1-{SP)-2-[2-(diphenylphosphino)phenyl] ferrocenyl}ethyldi(2-norbonyl)phosphine; (R)-1-{(RP)-2-[2-(diphenylphosphino)phenyl]ferrocenyl}ethyldi(3,5-xylyl)phosphine; (S)-1-{(SP)-2-[2-(diphenylphosphino) phenyl]ferrocenyl}ethyldi(3,5-xylyl)phosphine; (R)-1-{ (RP)-2-[2-[di(3,5-xylyl)phosphino]phenyl] ferrocenyl}ethyldi(3,5-xylyl)phosphine; (S)-1-{(SP)-2-[2-[di(3,5-xylyl)phosphino]phenyl]ferrocenyl}ethyldi(3,5-xylyl)phosphine; (R)-1-{(RP)-2-[2-(diphenylphosphino) phenyl]ferrocenyl}ethylbis[3,5-bis-(trifluoromethyl)phenyl] phosphine; (S)-1-{(SP)-2-[2-(diphenylphosphino)phenyl] ferrocenyl}ethylbis[3,5-bis-(trifluoromethyl)phenyl] phosphine; (R)-1-{(RP)-2-[2-[bis(4-methoxy-3,5-dimethylphenyl)phosphino]phenyl]ferrocenyl}ethylbis[3,5-bis(trifluoromethyl)phenyl]phosphine; (S)-1-{(SP)-2-[2-[bis (4-methoxy-3,5-dimethylphenyl)phosphino]phenyl] ferrocenyl}ethylbis[3,5-bis(trifluoromethyl)phenyl] phosphine; 3,3',4,4'-tetramethyl-1,1'-diphenyl-2,2',5,5'-tetrahydro-1H,1'H-2,2'-biphosphol; 1,1'-di-tert-butyl-2, 2'biphospholane; 2,2'-di-tert-butyl-2,2',3,3'-tetrahydro-1H, 1'H-1,1'-bisisophosphoindole; 1,2-bis(2,4-dimethylphosphetan-1-yl)ethane; 1,2-bis(2,5-dimethylphosphoran-1-yl)ethane; 1,2-bis(2,4-dimethylphosphetan-1-yl)benzene; 1,2-bis(2,5-dimethylphosphoran-1-yl)benzene; 3,4-bis(2,5-dimethylphosphoran-1-yl)furan-2,5-dione; 3,4-bis(2,5-diethylphosphoran-1-yl) furan-2,5-dione; 3,4-bis(2,5-dimethylphosphoran-1-yl)-1-phenyl-1H-pyrrole-2,5-dione; 1-(3,5-bis(trifluoromethyl)phenyl)-3,4-bis(2,5-dimethylphosphoran-1-yl)-1H-pyrrole-2,5-dione; 1-((1R,2S,4R, 5S)-2,5-dimethyl-7-phosphabicyclo[2.2.1]heptan-7-yl)-2-((2R,5S)-2,5-dimethyl-7-phosphabicyclo[2.2.1]heptan-7-yl) benzene; 1,1'-(benzo[b]thiophene-2,3-diyl)bis(2,5-dimethylphospholane); (2,2',4,4'-tetramethyl-3,3',4,4'-tetrahydro-2H,2'H-6,6'-bibenzo[b][1,4]dioxepin-7,7'-diyl) bis(diphenylphosphine); (2,2',4,4'-tetramethyl-3,3',4,4'-tetrahydro-2H,2'H-6,6'-bibenzo[b][1,4]dioxepin-7,7'-diyl) bis(di(3,5-xylyl)phosphine); ((6R)-6,7-dimethyl-6,7-dihydrodibenzo[e,g][1,4]dioxosin-1,12-diyl)bis (diphenylphosphine); ((6R)-6,7-dimethyl-6,7-dihydrodibenzo[e,g][1,4]dioxosin-1,12-diyl)bis(di(3,5-xylyl)phosphine); (4,4',5,5',6,6'-hexamethylbiphenyl-2,2'-diyl)bis(diphenylphosphine); (4,4',5,5',6,6'-hexamethylbiphenyl-2,2'-diyl)bis(di(3,5-xylyl)phosphine);

(4,4',5,5',6,6'-hexamethoxybiphenyl-2,2'-diyl)bis(diphenylphosphine); (4,4',5,5',6,6'-hexamethoxybiphenyl-2,2'-diyl)bis(di(3,5-xylyl)phosphine); (5,5'-dichloro-4,4',6,6'-tetramethylbiphenyl-2,2'-diyl)bis(diphenylphosphine); (5,5'-dichloro-4,4',6,6'-tetramethylbiphenyl-2,2'-diyl)bis(di(3,5-xylyl)phosphine); (5,5'-dimethoxy-4,4',6,6'-tetramethylbiphenyl-2,2'-diyl)bis(diphenylphosphine); (5,5'-dimethoxy-4,4',6,6'-tetramethylbiphenyl-2,2'-diyl)bis(di(3,5-xylyl)phosphine); 2,2'-bis(diphenylphosphino)-6,6'-dimethoxybiphenyl-3,3'-diol; 2,2'-bis(di(3,5-xylyl)phosphino)-6,6'-dimethoxybiphenyl-3,3'-diol; (3,3',6,6'-tetramethoxybiphenyl-2,2'-diyl)bis(diphenylphosphine); (3,3',6,6'-tetramethoxybiphenyl-2,2'-diyl)bis(di(3,5-xylyl)phosphine); (3,3'-diisopropyl-6,6'-dimethoxybiphenyl-2,2'-diyl)bis(diphenylphosphine); (3,3'-diisopropyl-6,6'-dimethoxybiphenyl-2,2'-diyl)bis(di(3,5-xylyl)phosphine); (6,6'-dimethoxy-3,3'-bis(p-tolyloxy)biphenyl-2,2'-diyl)bis(diphenylphosphine); (6,6'-dimethoxy-3,3'-bis(p-tolyloxy)biphenyl-2,2'-diyl)bis(di(3,5-xylyl)phosphine); 2,2'-bis(diphenylphosphino)-6,6'-dimethoxybiphenyl-3,3'-diyl bis(2,2-dimethylpropanoate); 2,2'-bis(di(3,5-xylyl)phosphino)-6,6'-dimethoxybiphenyl-3,3'-diylbis(2,2-dimethylpropanoate); (5,5'-dichloro-6,6'-dimethoxybiphenyl-2,2'-diyl)bis(diphenylphosphine); (5,5'-dichloro-6,6'-dimethoxybiphenyl-2,2'-diyl)bis(di(3,5-xylyl)phosphine); 6,6'-bis(diphenylphosphino)biphenyl-2,2'-diyl diacetate; 6,6'-bis(di(3,5-xylyl)phosphino)biphenyl-2,2'-diyl diacetate; 6,6'-bis(diphenylphosphino)biphenyl-2,2'-diylbis(2,2-dimethylpropanoate); 6,6'-bis(di(3,5-xylyl)phosphino)biphenyl-2,2'-diylbis(2,2-dimethylpropanoate); 6,6'-bis(diphenylphosphino)biphenyl-2,2'-diylbis(2-methylpropanoate); 6,6'-bis(di(3,5-xylyl)phosphino)biphenyl-2,2'-diylbis(2-methylpropanoate); 6,6'-bis(diphenylphosphino)biphenyl-2,2'-diyl dicyclohexane carboxylate; 6,6'-bis(di(3,5-xylyl)phosphino)biphenyl-2,2'-diyl dicyclohexane carboxylate; (4,4',6,6'-tetrakis(trifluoromethyl)biphenyl-2,2'-diyl)bis(diphenylphosphine); (4,4',6,6'-tetrakis(trifluoromethyl)biphenyl-2,2'-diyl)bis(di(3,5-xylyl)phosphine); (5-methoxy-4,6-dimethyl-4',6'-bis(trifluoromethyl)biphenyl-2,2'-diyl)bis(diphenylphosphine); (5-methoxy-4,6-dimethyl-4',6'-bis(trifluoromethyl)biphenyl-2,2'-diyl)bis(di(3,5-xylyl)phosphine); (2,2,2',2'-tetramethyl-4,4'-bibenzo[d][1,3]dioxol-5,5'-diyl)bis(diphenylphosphine); (2,2,2',2'-tetramethyl-4,4'-bibenzo[d][1,3]dioxol-5,5'-diyl)bis(di(3,5-xylyl)phosphine); 6,6'-bis(diphenylphosphino)-2,2',3,3'-tetrahydro-7,7'-bibenzofuran; 6,6'-bis(di(3,5-xylyl)phosphino)-2,2',3,3'-tetrahydro-7,7'-bibenzofuran; (2,2,2',2'-tetrafluoro-4,4'-bibenzo[d][1,3]dioxol-5,5'-diyl)bis(diphenylphosphine); (2,2,2',2'-tetrafluoro-4,4'-bibenzo[d][1,3]dioxol-5,5'-diyl)bis(di(3,5-xylyl)phosphine); 2-(naphthyl)-8-diphenylphosphino-1-[3,5-dioxa-4-phosphacyclohepta[2,1-a;3,4-a']dinaphthalene-4-yl]-1,2-dihydroquinoline; 4,12-bis(di(3,5-xylyl)phosphino)-[2.2]-paracyclophane; 7,7'-bis(di(3,5-xylyl)phosphino)-2,2',3,3'-tetrahydro-1,1'-spirobiindane (Xyl-SDP); 7,7'-bis(diphenylphosphino)-2,2',3,3'-tetrahydro-1,1'-spirobiindane (SDP); bis(2-diphenylphosphinophenyl) ether (DPEphos); 4,5-bis(diphenylphosphinomethyl)-2,2-dimethyl-1,3-dioxolan (DIOP); 1,2-bis(diphenylphosphino)propane (PROPHOS); 2,3-bis(diphenylphosphino)butane (CHIRAPHOS); 1,2-bis[(2-methoxyphenyl)(phenyl)phosphino]ethane (DIPAMP); 3,4-bis(diphenylphosphino)-1-benzylpyrrolidine (DEGUPHOS); 2,3-bis(diphenylphosphino)-bicyclo[2.2.1]hepto-5-ene (NORPHOS); 1-tertiary-butoxycarbonyl-4-diphenylphosphino-2-(diphenylphosphinomethyl)pyrrolidine (BPPM); (2,2'-bis-(dibenzofuran-3,3-diyl)-bis-diphenylphosphine (BIBFUP); 2,2'-bis(diphenylphosphino)-3,3'-binaphtho[b]furan (BINAPFu); 2,2'-bis(diphenylphosphino)-3,3'-bi[benzo[b]thiophene] (BITIANP); N,N'-dimethyl-7,7'-bis(di(3,5-xylyl)phosphino)-3,3',4,4'-tetrahydro-8,8'-bi-2H-1,4-benzoxazine (Xyl-Solphos); 2,3-bis(tertiary-butylmethylphosphino) quinoxaline (QuinoxP*); 2,4-bis(diphenylphosphino)pentane (SKEWPHOS); 2,4-bis(di(3,5-xylyl)phosphino)pentane (XylSKEWPHOS); 4,4'-bis(diphenylphosphino)-2,2',5,5'-tetramethyl-3,3'-bithiophene (TMBTP); 3,3'-bis(diphenylphosphonyl)-1,1'-2,2'-biindole (N-Me-2-BINPO); (2,2',5,5'-tetramethyl-3,3'-bithiophene-4,4'-diyl)bis(diphenylphosphine) (BITIANP); (4,4',6,6'-tetramethyl-3,3'-bibenzo[b]thiophene-2,2'-diyl)bis(diphenylphosphine) (tetraMe-BITIANP); 1,1'-bis(diphenylphosphino)-3,3'-dimethyl-1H,1'H-2,2'-biindole (BISCAP); 2,2'-bis(diphenylphosphino)-3,3'-bibenzofuran (BICUMP) and 2,2'-bis(diphenylphosphino)-1,1'-bibenzo[d]imidazole (BIMIP).

The diphosphine which can be used for the invention as specifically exemplified in the above may be an optically active diphosphine.

Next, a method for preparing the ruthenium complex of the invention will be explained.

The ruthenium complex of the invention can be prepared by the ruthenium compound represented as Formula (A) reacting with diamine compound. Otherwise, the ruthenium complex of the invention can be prepared by the ruthenium compound represented as Formula (B) reacting with a diphosphine compound represented by P⌒P and then with the diamine compound.

The ruthenium compound represented as Formula (B) (hereinafter, referred to as an arene complex) is the commercial product, or can be prepared according to a known method. Otherwise, the ruthenium compound represented as Formula (A)(hereinafter, referred to as an arene-phosphine complex) is the commercial product, or can be prepared by the arene complex represented as Formula (B) reacting with a diphosphine compound represented by P⌒P, according to a known method.

The examples of the arene represented as L in Formula (A) or Formula (B) include $C_6$-$C_{20}$ aromatic compound which may have a substituent complexible for ruthenium atom, preferably cyclic aromatic compound. The example of the preferably arene includes benzene; o-, m-, or p-xylene; o-, m-, or p-cymene; trimethyl benzene, such as mesitylene. The preferable examples of the ruthenium compound represented as Formula (B) include the ruthenium compound coordinating with an aromatic compound such as $[RuCl_2(benzene)]_2$, $[RuCl_2(p\text{-cymene})]_2$, and $[RuCl_2(mesitylene)]_2$. Otherwise, the preferable example of the ruthenium compound represented as Formula (A) include the ruthenium compound coordinating with a aromatic compound such as [RuCl(benzene)(P⌒P)]Cl, [RuCl(p-cymene)(P⌒P)]Cl and [RuCl(mesitylene)(P⌒P)]Cl.

The examples of the diamine compound include the diamine compound having tow endmost amino group that more than one of the amino groups have an α-substituent of aryl group, the preferably diamine compound represented by the following Formula (8)

[Chem. 13]

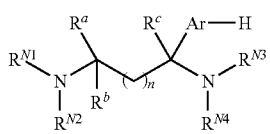

(8)

(in the formula, $R^a$, $R^b$ and $R^c$ each independently represent a hydrogen atom, an optionally substituted $C_1$-$C_{20}$ alkyl group, or an optionally substituted $C_2$-$C_{20}$ alkenyl group, or an optionally substituted $C_3$-$C_8$ cycloalkyl group, or an optionally substituted $C_7$-$C_{20}$ aralkyl group, or an optionally substituted aryl group, or an optionally substituted heterocyclic group or $R^b$ and $R^c$ may be form an alkylene group or an alkylenedioxy group; $R^{N1}$, $R^{N2}$, $R^{N3}$ and $R^{N4}$ each independently represent a hydrogen atom, an optionally substituted $C_1$-$C_{20}$ alkyl group, an optionally substituted $C_2$-$C_{20}$ alkenyl group, an optionally substituted $C_7$-$C_{20}$ aralkyl group, or an optionally substituted $C_3$-$C_8$ cycloalkyl group, and at least one of $R^{N1}$, $R^{N2}$, $R^{N3}$ and $R^{N4}$ represents a hydrogen atom; or $R^{N1}$ and $R^a$ may form alkylene group, and n is an integer of 0 to 3 and Ar represents an optionally substituted arylene group.)

Meanings of the each symbol of the substituent group included in the Formula (8) are the same as those described above.

Specific examples of the diamine compound represented by the Formula (8) used in the invention include 1,2-diphenylethylenediamine; 1,2-bis(4-methoxyphenyl)ethylenediamine; 1-methyl-2,2-diphenylethylenediamine; 1-isobutyl-2,2-diphenylethylenediamine; 1-isopropyl-2,2-diphenylethylenediamine (DPIPEN); 1-methyl-2,2-bis(4-methoxyphenyl)ethylenediamine (DAMEN); 1-isobutyl-2,2-bis(4-methoxyphenyl)ethylenediamine; 1-isopropyl-2,2-bis(4-methoxyphenyl)ethylenediamine (DAIPEN); 1-phenyl-2,2-bis(4-methoxyphenyl)ethylenediamine; 1,1-diphenylethylenediamine (1,1-DPEN); 1,1-bis(4-methoxyphenyl)ethylenediamine (DAEN); and 1-isopropyl-2,2-bis(3-methoxyphenyl)ethylenediamine (3-DAIPEN). These diamine compounds may be an optically active diamine compound. In the case of optically active diamine compound, there is (R) or (S) at the ahead of its name to show the optically activity.

Specifically, the method for preparing the ruthenium complex of the invention is as follows.

The method for preparing an arene-phosphine complex is described, see e.g. J. CHEM. SOC., CHEM. COMMUN 1208 (1989), and by reacting the arene-phosphine complex present as the prepared solution or as a solid matter obtained after crystallization, and solvent drying, etc. with the diamine compound represented by the Formula (8) in an amount of at least one equivalent, preferably 1 to 20 equivalents, more preferably 1 to 10 equivalents, and still more preferably 1.1 to 5 equivalents relative to the arene-phosphine complex, the ruthenium complex of the invention can be obtained. In addition, the preparation method of the invention is carried out in the presence of an alcohol, and the alcohol may be used singly or in combination with other solvent Examples of the alcohol used herein include a lower alkanol such as methanol, ethanol, n-propanol, 2-propanol and n-butanol. Preferred examples of alcohol include methanol and ethanol. In addition, although an additive is not necessarily required, by adding 01 to 2 equivalents, preferably 0.5 to 1.5 equivalents and more preferably 0.9 to 1.1 equivalents of a base relative to the arene-phosphine complex, the complex can be efficiently produced.

Thus, the invention provides a method for preparing the ruthenium complex represented by the Formula (1) by reacting the arene-phosphine complex and the diamine compound represented by the Formula (8) in the presence of a lower alcohol. More specifically, the method of the invention is carried out in the presence of a base, in particular an organic base.

As a base, an inorganic base and an organic base can be mentioned. Examples of an inorganic base include potassium carbonate ($K_2CO_3$), lithium hydroxide (LiOH), sodium hydrogen carbonate ($NaHCO_3$), sodium carbonate ($Na_2CO_3$), potassium hydrogen carbonate ($KHCO_3$), potassium methoxide ($KOCH_3$), sodium methoxide ($NaOCH_3$), lithium methoxide ($LiOCH_3$), sodium ethoxide ($NaOCH_2CH_3$), sodium acetate ($CH_3CO_2Na$), potassium isopropoxide ($KOCH(CH_3)_2$), potassium tert-butoxide ($KOC(CH_3)_3$), potassium naphthalenide ($KC_{10}H_8$), cesium carbonate ($Cs_2CO_3$) and silver carbonate ($Ag_2CO_3$). Examples of an organic base include organic amines such as triethylamine, diethylamine, diisopropylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undeca-7-ene, tri-n-butylamine and N-methylmorpholine.

As a catalyst for asymmetric reduction, the ruthenium complex of the invention has an excellent catalytic activity. By using the ruthenium complex of the invention as a catalyst for asymmetric reduction, alcohols can be produced by asymmetric reduction of a carbonyl group. Examples of the carbonyl group for the preparation method of the invention include a carbon/oxygen double bond such as a keto group and an ester group. Preferable carbonyl group includes a keto group. In particular, as being in excellent in terms of enantioselectivity, etc., the catalyst for asymmetric reduction of the invention is suitable for a method for producing optically active alcohols from a prochiral keto group.

The method for preparing alcohols of the invention can be preferably carried out with or without a solvent. However, it is preferably carried out by in the presence of a solvent. As for the solvent used, those which can dissolve a substrate and a catalyst are preferable, and a single solvent or a mixture solvent is used. Specific examples include an aromatic hydrocarbon such as toluene and xylene, an aliphatic hydrocarbon such as hexane and heptane, a halogenated hydrocarbon such as methylene chloride and chlorobenzene, an ether such as diethyl ether, tetrahydrofuran, methyl tert-butyl ether and cyclopentylmethyl ether, an alcohol such as methanol, ethanol, 2-propanol, n-butyl alcohol, 2-butanol and tert-butyl alcohol, and a polyol such as ethylene glycol, propylene glycol, 1,2-propanediol and glycerin. Among these, an ether or an alcohol is preferable. Particularly preferred solvents include tetrahydrofuran, methanol, ethanol and 2-propanol. Use amount of the solvent can be appropriately selected depending on reaction condition, etc. The reaction is carried out under stirring, if necessary.

The use amount of the catalyst varies with the reduced substrate, a reaction condition or type of a catalyst, etc., but it is generally in the range of 0.00001 mol % to 1 mol %, and preferably 0.0001 mol % to 0.5 mol % in terms of the molar ratio of the ruthenium metal relative to the substrate to be reduced.

Moreover, the asymmetric reduction of the invention is preferably carried out by adding a base compound Examples of the base compound to be used include an inorganic base and an organic base. Examples of the inorganic base include potassium carbonate ($K_2CO_3$), potassium hydroxide (KOH), lithium hydroxide (LiOH), sodium hydrogen carbonate ($NaHCO_3$), sodium carbonate ($Na_2CO_3$), potassium hydrogen carbonate ($KHCO_3$), and sodium hydroxide (NaOH). Examples of the organic base include an alkali-alkali earth metal salt such as potassium methoxide ($KOCH_3$), sodium methoxide ($NaOCH_3$), lithium methoxide ($LiOCH_3$), sodium ethoxide ($NaOCH_2CH_3$), potassium isopropoxide ($KOCH(CH_3)_2$), potassium tert-butoxide ($KOC(CH_3)_3$), and potassium naphthalenide ($KC_{10}H_8$) and an organic amine such as triethylamine, diethylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undeca-7-ene, tri-n-butylamine and N-methylmorpholine. In addition, the base to be used in the invention can be metal hydrides such as sodium hydride and potassium hydride. In addition, the base to be used in the invention is not limited to the bases described above, and hydrogen and others that can generate an amine-phosphine ruthenium hydride complex can be used. These bases can be used singly or in appropriate combination of two or more. Preferred examples of the base compound include an inorganic base and an alkali-alkali earth metal salt.

The use amount of the base compound is 1 to 10000 equivalents, and preferably 10 to 5000 equivalents compared to the mole number of the ruthenium complex, or it is in the range of 0.00001 mol % to 50 mol %, and preferably 0.0001 mol % to 30 mol % in terms of the molar ratio of the base compound relative to the substrate to be reduced.

With regard to the method of the invention, the reaction temperature for carrying out asymmetric hydrogenation as asymmetric reduction is −30° C. to 100° C., and preferably 0° C. to 50° C. If the reaction temperature is too low, large amount of raw materials may remain unreacted. On the other hand, if it is too high, raw materials and the catalyst may decompose, and therefore undesirable. The present invention is also characterized in that the asymmetric hydrogenation can be carried out at low temperature, for example −30 to 30° C.

With regard to the invention, as the catalytic system has an extremely high activity, the hydrogen pressure as atmospheric pressure (0.1 MPa) which is enough for carrying out the asymmetric hydrogenation. However, it is preferably 0.1 MPa to 10 MPa, more preferably 0.1 MPa to 6 MPa, and still more preferably 0.1 MPa to 3 MPa. Furthermore, the reaction time is 1 minute to 72 hours, and preferably 30 minutes to 48 hours to obtain sufficiently high conversion rate of raw materials.

With regard to the asymmetric reduction of the invention, an asymmetric hydrogen-transfer reduction is carried out by reacting the ruthenium complex of the invention in the presence of a hydrogen donor. The hydrogen donor is not specifically limited if it was generally used for hydrogen-transfer reduction, including formic acid or its salt, and an alcohol in which a hydrogen atom is present at a position of the carbon atom substituted with a hydroxy group, i.e., 2-propanol. However, combination of 2-propanol and a base compound is preferable. The examples the base which can be used herein include a tertiary organic amines such as trimethylamine, triethylamine and triisopropylamine and an inorganic base such as LiOH, NaOH, KOH and $K_2CO_3$. The base is used in an excess amount compared to the ruthenium complex, for example, 1 to 10,000 times in molar ratio.

If the hydrogen donor is liquid, it can be generally used as a solvent for the reaction. However, it is also possible to use a non-hydrogen donor solvent such as toluene, tetrahydrofuran, acetonitrile, dimethyl formamide and dimethyl sulfoxide as a co-solvent, either singly or as a mixture for dissolving raw materials.

The use amount of the ruthenium complex as a catalyst is generally selected within the range of 0.000001 mol % to 5 mol %, and preferably 0.0001 mol % to 2 mol % in terms of molar ratio of the ruthenium complex compared to the substrate to be reduced.

The use amount of the hydrogen donor compared to the substrate to be reduced is generally the same molar amount or more, and when the hydrogen donor is formic acid or its salt, it is preferably used within the range of 1.5 times molar amounts or more, and also 20 times molar amounts or less, and preferably 10 times molar amounts or less. On the other hand, when the hydrogen donor is 2-propanol or the like, the hydrogen donor is used in a large excess with respect to the substrate from the viewpoint of reaction equilibrium, and is usually used in a 1000-fold molar amount or less.

The reaction temperature is selected within the range of −70 to 100° C., and preferably 0 to 70° C.

The reaction pressure is not specifically limited, and it is generally 0.05 to 0.2 MPa, preferably atmospheric pressure.

The reaction time is 0.5 to 100 hours, and generally 1 to 50 hours.

After the reaction is completed, a purification method which is generally used, for example, extraction, filtration, crystallization, distillation and various chromatographies, is carried out either singly or in appropriate combination to obtain desired alcohols.

EXAMPLES

Hereinafter, the Examples are described and the invention will be described in greater detail. However, the invention is not limited by the following Examples.

Measurement of $^1$H-NMR spectrum and $^{31}$P-NMR spectrum was carried out by using MERCURY plus 300 manufactured by Varian, Inc., and the MS measurement was carried out by using JMS-T100GCV manufactured by JEOL or LCMS-IT-TOF manufactured by Shimadzu Corporation.

Example 1

Preparation of RuCl[(S)-xylbinap][(S)-daipen]

[Chem. 14]

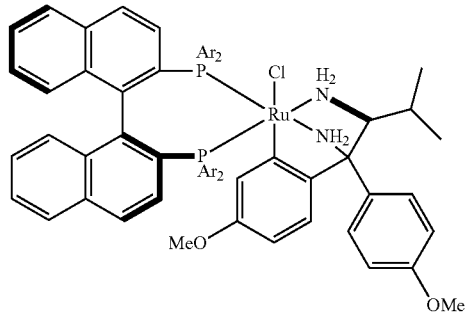

-continued

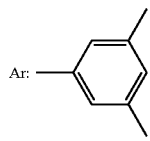

Under nitrogen gas, [RuCl$_2$(p-cymene)]$_2$ 3.07 g (5.0 mmol), (S)-XylBINAP 7.35 g (10.0 mmol) and methanol 110 mL were added to a 200 mL 4-neck flask. The mixture was heated to 50° C. and stirred for 2 hours to prepare [RuCl(p-cymene)((S)-xylbinap)]Cl. The reaction solution was cooling down to room temperature, then diethylamine 736 mg (10 mmol) and (S)-DAIPEN 3.48 g (11.1 mmol) were added to the reaction solution, and stirred for 3 hours at 60° C. After concentration, the residue was dissolved in butyl acetate and the precipitated salts were separated by filtration. The filtrate was concentrated and the mixture added with heptane (110 mL) was cooling down to −10° C. The precipitated crystals were filtered to obtain the title compound (11.62 g) with yield of 98%.

$^{31}$P-NMR (C$_6$D$_6$): δ
53.2 (d, J=38.6 Hz), 61.0 (d, J=38.6 Hz)
TOF-mass (IV): m/z=1184.3 (theoretical value: 1184.4)
ESI: m/z=1184.3967 (theoretical value: 1184.3890)
Elemental analysis (wt %) Ru, 8.6; P, 5.2; Cl, 3.1; H, 5.77; C, 71.48; N, 2.29; [measured value]
Elemental analysis (wt %) Ru, 8.5; P, 5.2; Cl, 3.0; H, 6.2; C, 72.0; N, 2.4; [calculated value]

Comparative Example 1

Preparation of trans-RuCl$_2$[(R)-xylbinap][(R)-daipen]

[Chem. 15]

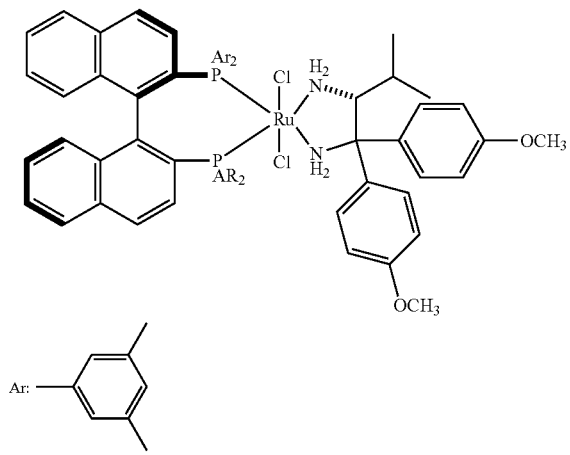

Under nitrogen gas, (R)-DAIPEN 314.4 mg (1 mmol) was added to the mixture of [RuCl(p-cymene)((R)-xylbinap)]Cl 1.04 g (1 mmol) and toluene 10 mL and stirred at 80° C. for 2 hours. The reaction solution was concentrated to obtain the title compound (1.2 g).

$^{31}$P-NMR (C$_6$D$_6$): δ
44.1 (d, J=37.3 Hz), 46.0 (d, J=37.3 Hz)
TOF-mass (FD): m/z=1220.3 (theoretical value: 1221.9)
Elemental analysis (wt %) Ru, 8.1; P, 4.6; Cl, 5.9; H, 5.81; C, 69.86; N, 2.21; [measured value]

Elemental analysis (wt %) Ru, 83; P, 5.1; Cl, 5.8; H, 6.1; C, 69.8; N, 2.3; [ calculated value]

Example 2

Preparation of RuCl[(R)-xylbinap][(R)-daipen]

[Chem. 16]

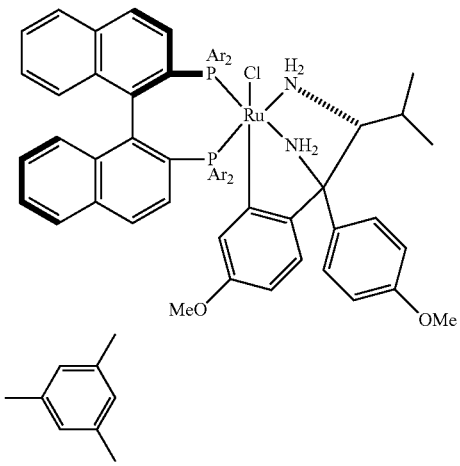

Except that (S)-XylBINAP was changed to (R)-XylBINAP and (S)-DAIPEN was changed to (R)-DAIPEN, the experiment was carried out in the same manner as Example 1 to obtain the title compound with yield of 98%.

Example 3

Preparation of RuCl[(R)-dm-segphos][(R)-daipen]

[Chem. 17]

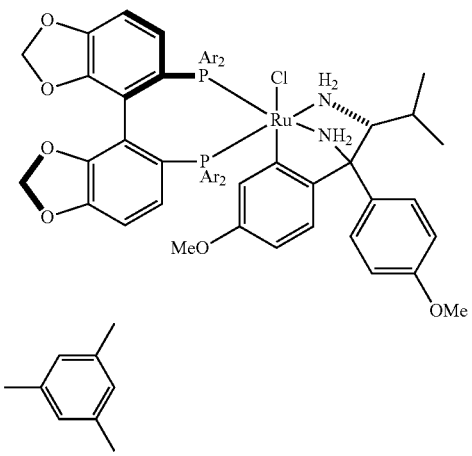

Under nitrogen gas, [RuCl$_2$(p-cymene)]$_2$ 4.24 g (6.92 mmol), (R)-DM-SEGPHOS 10.00 g (13.83 mmol) and methanol 200 mL were added to a 300 mL 4-neck flask. The mixture was heated to 50° C. and stirred for 2 hours. The reaction solution was cooling down to room temperature, triethylamine 1.40 g (13.8 mmol) and (R)-DAIPEN 6.52 g (20.7 mol) were added to the reaction solution, and stirred for 20 hours at 45° C. The resulted reaction solution was cooled to −10° C. The precipitated crystals were filtered to obtain the title compound with yield of 59%.

$^{31}$P-NMR (CD$_2$Cl$_2$): δ
51.0 (d, J=37.3 Hz), 55.8 (d, J=37.4 Hz)
TOF-mass (ID): m/z=1172.3 (theoretical value: 1172.3)

Comparative Example 2

Preparation of trans-RuCl$_2$[(R)-dm-segphos][(R)-daipen]

[Chem. 18]

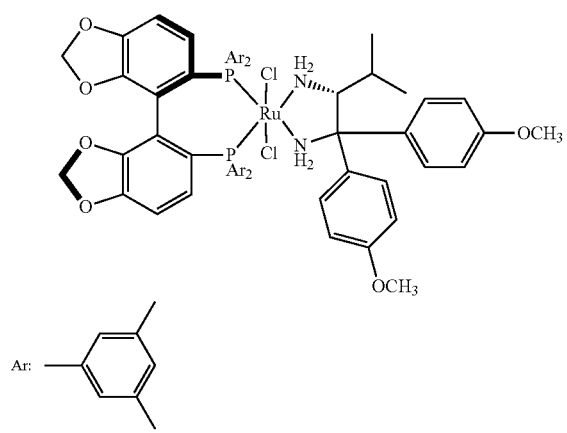

Under nitrogen gas, (R)-DAIPEN 314.4 mg (1 mmol) was added to the mixture of [RuCl(p-cymene)((R)-dm-segphos)]Cl 1.03 g (1 mmol) and toluene 10 mL and stirred at 80° C. for 2 hours. The reaction solution was concentrated to obtain the title compound (1.2 g).
$^{31}$P-NMR(C$_6$D$_6$): δ
46.3 (d, J=37.4 Hz), 47.0 (d, J=38.6 Hz)

As shown in Comparative examples 1 and 2, when the diamine compound is reacted in the absence of an alcohol, only the trans form having no Ru-carbon bond was produced.

Example 4

Preparation of RuI[(S)-xylbinap][(S)-daipen]

[Chem. 19]

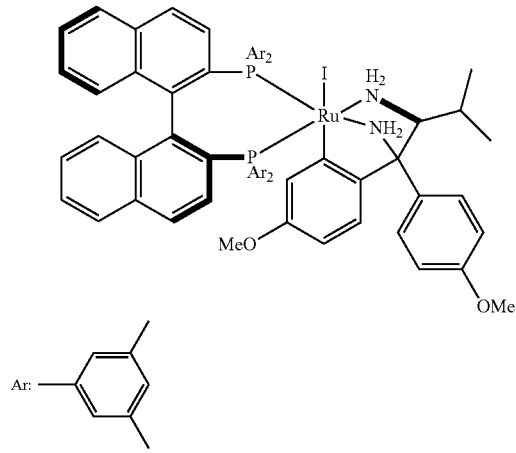

Except that [RuCl$_2$(p-cymene)]$_2$ was changed to [RuI$_2$(p-cymene)]$_2$, the experiment was carried out in the same manner as Example 1 to obtain the title compound with yield of 55%.

$^{31}$P NMR (C$_6$D$_6$): δ
53.2 (d, J=38.6 Hz), 62.6 (d, J=38.7 Hz)

Example 5

Preparation of RuCl[(R)-dm-segphos][(S)-daipen]

[Chem. 20]

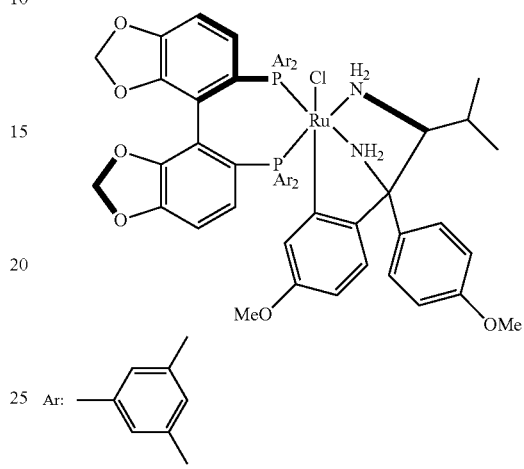

Except that (R)-DAIPEN was changed to (S)-DAIPEN, the experiment was carried out in the same manner as Example 3 to obtain the title compound with yield of 60%.

$^{31}$P NMR (C$_6$D$_6$): δ
52.6 (d, J=38.7 Hz), 57.5 (d, J=38.6 Hz)

Example 6

Preparation of RuI[(R)-dm-segphos][(R)-daipen]

[Chem. 21]

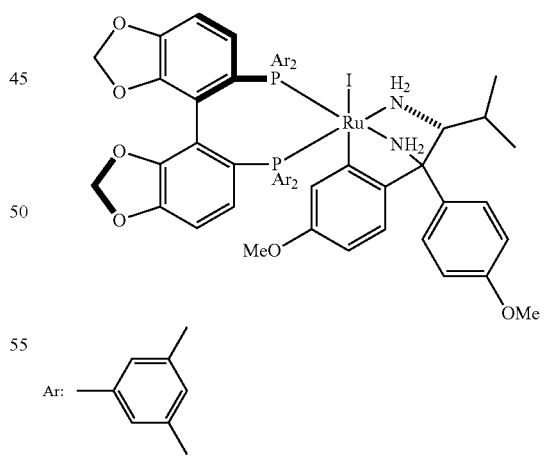

Except that [RuCl$_2$(p-cymene)]$_2$ was changed to [RuI$_2$(p-cymene)]$_2$, the experiment was carried out in the same manner as Example 3 to obtain the title compound with yield of 50%.

$^{31}$P NMR (C$_6$D$_6$): δ
52.1 (d, J=38.7 Hz), 57.6 (d, J=38.7 Hz)

Example 7

Preparation of RuCl[(R)-segphos][(R)-daipen]

[Chem. 22]

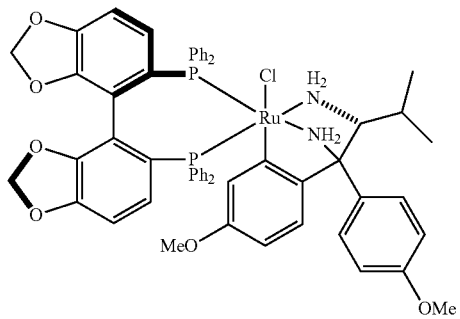

Under nitrogen gas, [RuCl$_2$(p-cymene)]$_2$ 153.1 mg (0.25 mmol), (R)-SEGPHOS 3053 mg (0.5 mmol), ethanol 18 mL and toluene 15 mL were added to a 50 mL 4-neck flask. The mixture was heated to 50° C. and stiffed for 2 hours. The reaction solution was cooling down to room temperature, a mixture of (R)-DAIPEN 471 mg (1.50 mmol) and ethanol 4 mL was added dropwise to the reaction solution, and then stirred for 20 hours at the same temperature. The resulted reaction solution was cooled to −20° C. The precipitated crystals were filtered to obtain the title compound with yield of 36%.

$^{31}$P-NMR (CD$_2$Cl$_2$): δ
53.0 (d, J=38.7 Hz), 57.7 (d, J=38.7 Hz)
TOF-mass (FD): m/z=1060.8 (theoretical value: 1060.2)

Example 8

Preparation of RuCl[(S)-xylbinap][(S)-damen]

[Chem. 23]

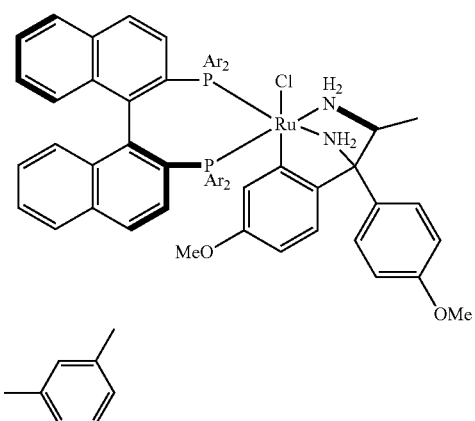

Under nitrogen gas, a mixture of [RuCl$_2$(p-cymene)]$_2$ 612.8 mg (1.0 mmol), (S)-XylBINAP 1.47 g (2.0 mmol) and methanol 15 mL was heated to 50° C. and stirred for 2 hours to prepare [RuCl(p-cymene)((S)-xylbinap)]Cl. The reaction solution was cooling down to room temperature, diethylamine 147 mg (2 mmol) and (S)-1,1-bis(4-methoxyphenyl)propane-1,2-diamine (hereinafter, referred to as (S)-DAMEN) 0.86 g (3.0 mmol) were added to the reaction solution, and then stirred for 3 hours at 60° C. The resulted reaction solution was concentrated and purified by silica gel column chromatography to obtain the title compound with yield of 59% (1.35 g).

$^{31}$P-NMR(C$_6$D$_6$): δ
54.4 (d, J=38.7 Hz), 61.8 (d, J=38.7 Hz)

Example 9

Preparation of RuCl[(S)-xylyl-meo-biphep][(S)-daipen]

[Chem. 24]

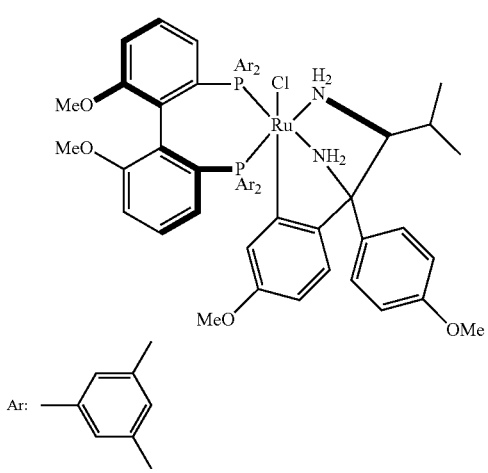

Under nitrogen gas, a mixture of [RuCl$_2$(p-cymene)]$_2$ 44.0 mg (0.072 mmol), (S)-Xylyl-MeO-BIPHEP 99.8 mg (0.144 mmol) and methanol 3 mL was heated to 50° C. and stirred for 2 hours to prepare [RuCl(p-cymene)((S)-xylyl-meo-biphep)]Cl. The reaction solution was cooling down to room temperature, triethylamine 14.5 mg (0.14 mmol) and (S)-DAIPEN 67.9 mg (0.216 mmol) were added to the reaction solution, and then stirred for 9 hours at 60° C. The resulted reaction solution was concentrated and purified by silica gel column chromatography to obtain the title compound with yield of 63% (104.3 mg).

$^{31}$P-NMR (C$_6$D$_6$): δ
52.1 (d, J=38.7 Hz), 58.6 (d, J=39.9 Hz)
TOF-mass (1-13): m/z=1144

Example 10

Preparation of RuCl[(S)-xylyl-H8-binap][(S)-daipen]

[Chem. 25]

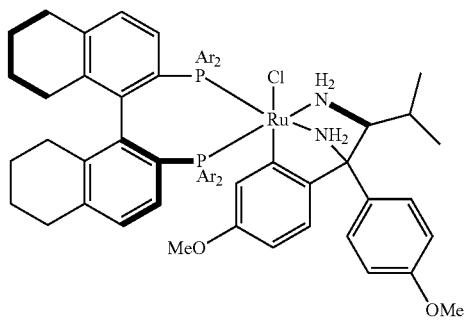

-continued

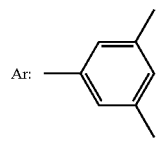
Ar:

Under nitrogen gas, a mixture of [RuCl$_2$(p-cymene)]$_2$ 61.2 mg (0.1 mmol), (S)-Xylyl-H8-BINAP 149.2 mg (0.2 mmol) and methanol 3 mL was heated to 50° C. and stirred for 2 hours to prepare [RuCl(p-cymene)((S)-xylyl-H8-binap)]Cl. The reaction solution was cooling down to room temperature, triethylamine 20.3 mg (0.2 mmol) and (S)-DAIPEN 94.3 mg (0.3 mmol) were added to the reaction solution, and then stirred for 8 hours at 60° C. The resulted reaction solution was concentrated and purified by silica gel column chromatography to obtain the title compound with yield of 46% (110.0 mg).

$^{31}$P-NMR (C$_6$D$_6$): δ
52.6 (d, J=39.9 Hz), 55.0 (d, J=39.6 Hz)

Example 11

Preparation of RuCl[(+)-xylyl-c3-tunephos][(S)-daipen]

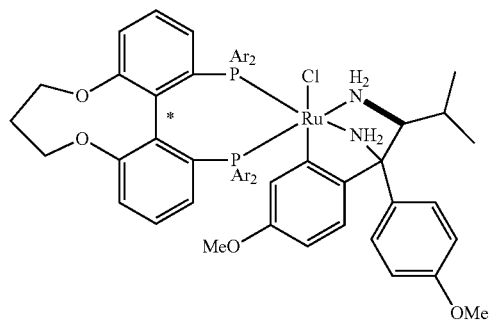

Ar:

Under nitrogen gas, a mixture of [RuCl$_2$(p-cymene)]$_2$ 61.2 mg (0.1 mmol), (+)-Xylyl-C$_3$-TUNEPHOS 141.4 mg (0.2 mmol) and methanol 3 mL was heated to 50° C. and stirred for 2 hours to prepare [RuCl(p-cymene)((+)-xylyl-c3-tunephos)]Cl. The reaction solution was cooling down to room temperature, triethylamine 20.3 mg (0.2 mmol) and (S)-DAIPEN 95.1 mg (0.3 mmol) were added to the reaction solution, and then stirred for 8 hours at 60° C. The resulted reaction solution was concentrated and purified by silica gel column chromatography to obtain the title compound with yield of 58% (134.1 mg).

$^{31}$P-NMR (C$_6$D$_6$): δ
53.6 (d, J=38.7 Hz), 57.5 (d, J=38.6 Hz)

Example 12

Preparation of RuCl[(R)-xylyl-synphos][(R)-daipen]

[Chem. 27]

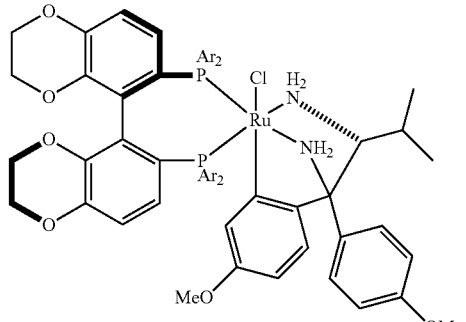

Ar:

Under nitrogen gas, a mixture of [RuCl$_2$(p-cymene)]$_2$ 61.2 mg (0.1 mmol), (R)-Xylyl-SYNPHOS 150.3 mg (0.2 mmol) and methanol 3 mL was heated to 50° C. and stirred for 2 hours to prepare [RuCl(p-cymene)((R)-xylyl-synphos)]Cl. The reaction solution was cooling down to room temperature, triethylamine 20.3 mg (0.2 mmol) and (R)-DAIPEN 95.0 mg (0.3 mmol) were added to the reaction solution, and then stirred for 8 hours at 60° C. The resulted reaction solution was concentrated and purified by silica gel column chromatography to obtain the title compound with yield of 52% (124.9 mg).

$^{31}$P-NMR (Toluene-d$_8$): δ
52.0 (d, J=40.1 Hz), 57.5 (d, J=39.9 Hz)

Example 13

Preparation of RuCl[(S)-xylyl-p-phos][(S)-daipen]

[Chem. 28]

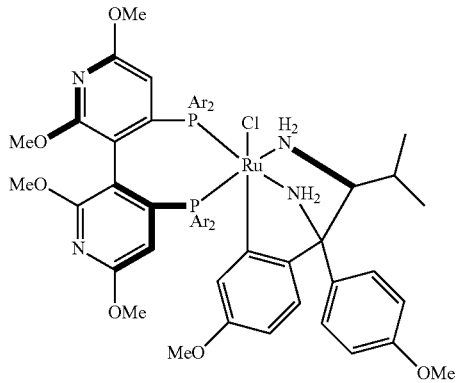

-continued

Ar: 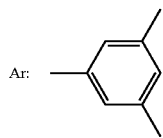

Under nitrogen gas, a mixture of [RuCl$_2$(p-cymene)]$_2$ 61.2 mg (0.1 mmol), (S)-Xylyl-P-Phos 151.5 mg (0.2 mmol) and methanol 3 mL was heated to 50° C. and stirred for 2 hours to prepare [RuCl(p-cymene)((R)-xylyl-P-phos)]Cl. The reaction solution was cooling down to room temperature, triethylamine 20.3 mg (0.2 mmol) and (S)-DAIPEN 95.1 mg (0.3 mmol) were added to the reaction solution, and then stirred for 6 hours at 60° C. The resulted reaction solution was concentrated and purified by silica gel column chromatography to obtain the title compound with yield of 62% (149.6 mg).

$^{31}$P-NMR (Toluene-d$_8$): δ

52.1 (d, J=38.6 Hz), 58.3 (d, J=39.9 Hz)

In the following examples, the conversion rate of 3-quinuclidinol was measured by gas chromatography (HP-1, injection temperature 250° C., detector temperature 250° C., initial column temperature 100° C. (maintained for 5 min.)—temperature elevation rate 10° C./min—final temperature 250° C.), and the optical purity (% ee) was measured by high performance chromatography (CHIRALPAK AD-H, eluent; hexane:2-propanol:diethylamine=90:10:0.1) following the benzoylation of a product.

Example 14

Preparation of (S)-3-quinuclidinol

To a 100 mL autoclave with a stirrer, 3-quinuclidinone (2.5 g, 20.0 mmol) and RuCl[(S)-xylbinap][(S)-daipen] (0.5 mg, 0.40 μmol, 1/50,000 molar fold of 3-quinuclidinone) obtained from the Example 1 above were added. After the autoclave was purged with nitrogen, 2-propanol (15 mL) and 2-propanol solution of potassium t-butoxide (0.1 mol/L, 1.0 mL, 0.1 mmol) were added. Subsequently, the autoclave was purged with hydrogen, the mixture was stirred at 30° C. for 6 hours under hydrogen pressure of 3 MPa. As a result of analysis of the reaction solution, it was found that the conversion rate is 99% or more and the optical purity is 912% ee.

Example 15

Preparation of (S)-3-quinuclidinol

Regarding Example 14, except that the reaction temperature was changed from 30° C. to 10° C., the same procedure as Example 14 was carried out. As a result of analysis of the reaction solution, it was found that the conversion rate is 99% or more and the optical purity is 94.6% ee.

Comparative Example 3

Preparation of (S)-3-quinuclidinol

To a 100 mL autoclave with a stirrer, 3-quinuclidinone (1.0 g, 8.0 mmol) and trans-RuCl$_2$[(S)-xylbinap][(S)-daiPen] (0.5 mg, 0.40 μmol, 1/20,000 molar fold of 3-quinuclidinone) were added. After the autoclave was purged with nitrogen, 2-propanol (6 mL) and 2-propanol solution of potassium t-butoxide (0.1 mol/L, 0.4 mL, 0.04 mmol) were added. Subsequently, the autoclave was purged with hydrogen, the mixture was stirred at 30° C. for 6 hours under hydrogen pressure of 3 MPa. As a result of analysis of the reaction solution, it was found that the conversion rate is 49.8% and the optical purity is 86.2° Me.

When Example 14 is compared to Comparative example 3, it was found that the catalytic activity of Comparative example 3 is only 1/5 or less of the catalytic activity of Example 14, and the optical purity of the product obtained is also low in Comparative example 3.

Example 16

Preparation of (R)-3-quinuclidinol

To a 100 mL autoclave with a stirrer, 3-quinuclidinone (2.5 g, 20.0 mmol) and RuCl[(R)-dm-segphos][(R)-daipen] obtained from Example 3 above (0.5 mg, 0.40 μmol, 1/50,000 molar equivalent fold of 3-quinuclidinone) were added. After purging with nitrogen, 2-propanol (15 mL) and 2-propanol solution of t-BuOK (0.1 mol/L, 1.0 mL, 0.1 mmol) were added. Subsequently, purging with hydrogen, the mixture was stirred at 30° C. for 6 hours under hydrogen pressure of 3 MPa. As a result of analysis of the reaction solution, it was found that the conversion rate is 99% or more and the optical purity is 91.1% et.

Example 17

Preparation of (R)-3-quinuclidinol

Regarding Example 16, except that the reaction temperature was changed from 30° C. to 10° C., the same procedure as Example 16 was carried out. As a result of analysis of the reaction solution, it was found that the conversion rate is 99% or more and the optical purity is 93.7% ee.

Comparative Example 4

Preparation of (R)-3-quinuclidinol

To a 100 mL autoclave with a stirrer, 3-quinuclidinone (1.0 g, 8.0 mmol) and trans-RuCl$_2$[(R)-dm-segphos][(R)-daipen] (0.5 mg, 0.40 μmol, 1/20,000 molar fold of 3-quinuclidinone) were added. After purging with nitrogen, 2-propanol (6 mL) and 2-propanol solution of t-BuOK (0.1 mol/L, 0.4 mL, 0.04 mmol) were added. Subsequently, the autoclave was purged with hydrogen, the mixture was stirred at 30° C. for 6 hours under hydrogen pressure of 3 MPa. As a result of analysis of the reaction solution, it was found that the conversion rate is 26.7% and the optical purity is 89.7% ee.

When Example 16 is compared to Comparative example 4, it was found that the catalytic activity of Comparative example 4 is only 1/5 or less of the catalytic activity of Example 16, and the optical purity of the product obtained is also low in Comparative example 4.

For the following examples, the conversion rate of 3-(methylamino)-1-(2-thienyl)propane-1-ol was measured by using high performance liquid chromatography (Inertsil ODS-SP, eluent; 1% aqueous solution of formic acid:water:methanol=5:90:5 to 5:5:90), and the optical purity (% ee) was measured by using high performance liquid chromatography (CHIRAL CD-Ph, eluent, 0.2 M sodium perchlorate:acetonitrile=30:70) following the benzoylation of a product.

Example 18

Preparation of (1S)-3-(methylamino)-1-(2-thienyl)propan-1-ol

Under nitrogen stream, 3-methylamino-1-thiophene-2-yl-propenone, RuCl[(R)-xylbinap][(R)-daipen] obtained from the Example 2 above (1/3000 molar fold of 3-methylamino-1-thiophene-2-yl-propenone) and lithium hydroxide (50 molar folds of the ruthenium catalyst) were added to an autoclave. Ethanol (3 mL per 1 g of 3-methylamino-1-thiophene-2-yl-propenone) was added, then the autoclave was purged with hydrogen and then stirred for 6 hours at 30° C. under hydrogen pressure of 4.5 MPa. As a result of analysis of the reaction mixture by HPLC, it was found that the conversion rate is 100%, selectivity is 993%, and the optical purity is 99% ee or more. In addition, the conversion rate and the selectivity were calculated according to the following equations.

Conversion rate: 100−(HPLC area % of the substrate)

Selectivity: (HPLC area % of the main product)/(100−(HPLC area % of the substrate))

Comparative Example 5

Regarding Example 18, except that RuCl[(R)-xylbinap][(R)-daipen] was changed to the same amount of trans-RuCl$_2$[(R)-xylbinap][(R)-daipen], the same procedure as Example 18 was carried out. As a result of analysis of the reaction mixture by HPLC, it was found that the optical purity is 99% ee or more, but the conversion rate is 83.9% and the selectivity is only 69.2%.

Example 19

Preparation of (1S)-3-(methylamino)-1-(2-thienyl)propan-1-ol

Regarding Example 18, except that the use amount of RuCl[(R)-xylbinap][(R)-daipen] was changed to 1/9000 molar fold of 3-methylamino-1-thiophene-2-yl-propenone, the same procedure as Example 18 was carried out. As a result of analysis of the reaction result by HPLC, it was found that the conversion rate is 99.3%, the selectivity is 95.0%, and the optical purity is 99% ee or more.

Example 20

Preparation of (S)-1-phenylethanol

Under nitrogen stream, acetophenone (20 mmol), RuCl[(S)-xylbinap][(S)-daipen] (1/100 molar fold of acetophenone) and t-BuOK (5 molar folds of the ruthenium catalyst) were added to a Schlenk tube. 2-propanol (8.3 mL per 100 mg of acetophenone) was added, then stirred for 10 minutes at 30° C. As a result of analysis of the reaction mixture by gas chromatography (Chirasil-DEX CB), it was found that the conversion rate is 94%, and the optical purity is 98.4% ee.

Example 21

Preparation of RuCl[(R)-tolbinap][(R)-daipen]

[Chem. 29]

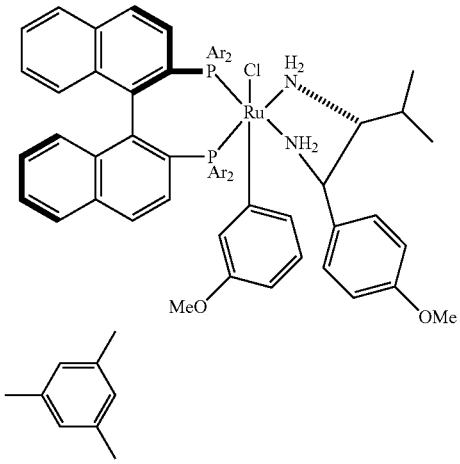

Under nitrogen gas, a mixture of [RuCl(p-cymene)((R)-tolbinap)]Cl 1.0 g (0.85 mmol), (R)-DAIPEN 440 mg (1.28 mmol), triethylamine 90 mg (0.94 mmol) and methanol 10 mL was stirred for 16 hours at 50° C. The reaction solution was concentrated and purified by silica gel column chromatography to obtain the title compound with yield of 26% (250 mg).

$^{31}$P-NMR (C$_6$D$_6$): δ
60.8 (d, J=39.9 Hz), 53.0 (J=39.9 Hz)

Example 22

Preparation of RuCl[(S)-xylbinap][daen]

[Chem. 30]

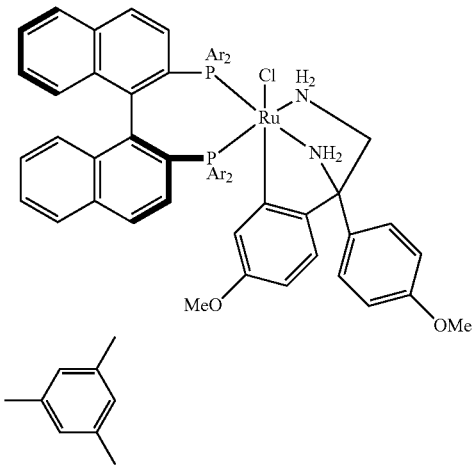

Under nitrogen gas, a mixture of [RuCl$_2$(p-cymene)]$_2$ 153.1 mg (0.25 mmol), (S)-XylBINAP 367.5 mg (0.50 mmol) and methanol 10 mL was heated to 55° C. and stirred for 2 hours to prepare [RuCl(p-cymene)((S)-xylbinap)]Cl. The reaction solution was cooling down to room temperature, diethylamine 36.6 mg (0.50 mmol), 1,1-bis(4-methoxyphenyl)ethylenediamine (hereinafter, referred to as DAEN) 149.8 mg (0.55 mmol) were added to the reaction solution, and then stirred for 15 hours at 55° C. The resulted reaction solution was cooled to 0° C. and the precipitated crystals were filtered to obtain the title compound with yield of 66% (377.6 mg).

$^{31}$P-NMR (C$_6$D$_6$): δ
55.0 (d, J=40.1 Hz), 61.3 (d, J=38.7 Hz)

Example 23

Preparation of RuCl[(S)-dm-segphos][daen]

[Chem. 31]

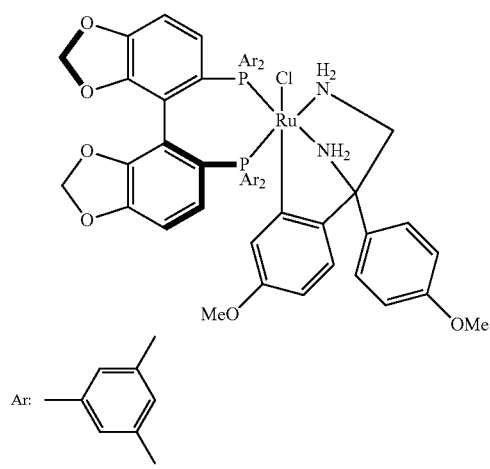

Ar: 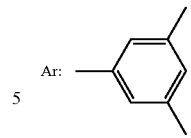

Except that (S)-XylBINAP was changed to (S)-DM-SEGPHOS, the experiment was carried out in the same manner as Example 23 to obtain the title compound with yield of 40% (225.5 mg).

$^{31}$P-NMR (C$_6$D$_6$): δ
54.2 (d, J=40.1 Hz), 57.5 (d, J=40.1 Hz)

Example 24

Preparation of RuCl[(S)-xylbinap][1,1-DPEN]

[Chem. 32]

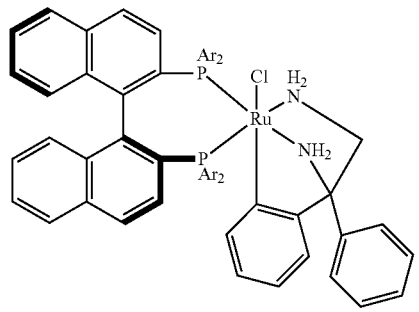

Except that DAEN was changed to 1,1-diphenylethylenediamine (hereinafter, referred to as 1,1-DPEN), the experiment was caned out in the same manner as Example 23 to obtain the title compound with yield of 77% (414.2 mg).

$^{31}$P-NMR (C$_6$D$_6$): δ
55.3 (d, J=38.9 Hz), 60.7 (d, J=40.1 Hz)

Example 25

Preparation of RuCl[(S)-binap][(S)-daipen]

[Chem. 33]

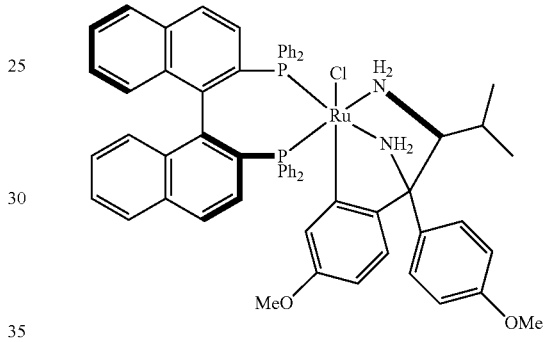

Under nitrogen gas, a mixture of [RuCl(p-cymene)((S)-binap)]Cl 1.0 g (1.08 mmol), (S)-DAIPEN 376.4 mg (1.18 mmol), diethylamine 80 mg (1.08 mmol) and methanol 10 mL was stirred for 20 hours at 50° C. The reaction solution was cooling down to 0° C. and the precipitated crystals were filtered to obtain the title compound with yield of 85% (982.5 mg).

$^{31}$P-NMR (C$_6$D$_6$): δ
54.6 (d, J=40.1 Hz), 62.0 (d, J=40.1 Hz)

Example 26

Preparation of RuCl[(S)-xylbinap][(S)-3-daipen]

[Chem. 34]

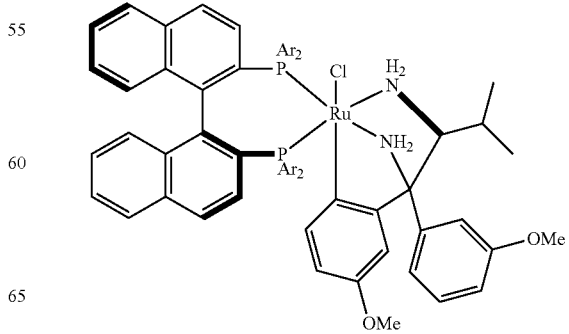

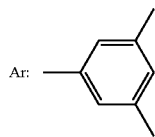

Under nitrogen gas, a mixture of [RuCl$_2$(p-cymene)]$_2$ 64.3 mg (0.11 mmol), (S)-XylBINAP 162 mg (0.22 mmol) and methanol 6 mL was heated to 50° C. and stirred for 2 hours to prepare [RuCl(p-cymene)((S)-xylbinap)]Cl. The reaction solution was cooling down to room temperature, diethylamine 16 mg (0.21 mmol) and (S)-1-isopropyl-2,2-bis(3-methoxyphenyl)ethylenediamine (hereinafter, referred to as (S)-3-DAIPEN) 72.3 mg (0.23 mmol) were added to the reaction solution, and then stirred for 20 hours at 50° C. The resulted reaction solution was concentrated and purified by silica gel column chromatography to obtain the title compound with yield of 44% (110 mg).

$^{31}$P-NMR (C$_6$D$_6$): δ
53.4 (d, J=38.8 Hz), 59.8 (d, J=38.8 Hz)

Example 27

Preparation of RuCl[(S)-xylbinap][(S)-dpipen]

[Chem. 35]

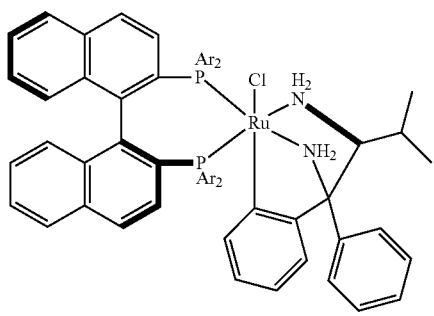

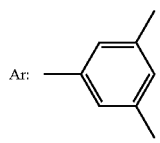

Under nitrogen gas, a mixture of [RuCl$_2$(p-cymene)]$_2$ 64.3 mg (0.11 mmol), (S)-XylBINAP 162 mg (0.22 mmol) and methanol 6 mL was heated to 50° C. and stirred for 2 hours to prepare [RuCl(p-cymene)((S)-xylbinap)]Cl. The reaction solution was cooling down to room temperature, diethylamine 16 mg (0.21 mmol) and (S)-1-isopropyl-2,2-diphenylethylenediamine (hereinafter, referred to as (S)-DPIPEN) 58.0 mg (0.23 mmol) were added to the reaction solution, and then stirred for 20 hours at 50° C. The resulted reaction solution was concentrated and purified by silica gel column chromatography to obtain the title compound with yield of 61% (150 mg).

$^{31}$P-NMR (C$_6$D$_6$): δ
53.0 (d, J=38.9 Hz), 59.7 (d, J=38.9 Hz)

Example 28

Preparation of Ru(OTf)[(S)-xylbinap][(S)-daipen]

[Chem. 36]

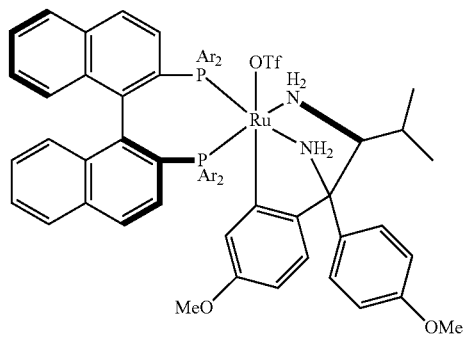

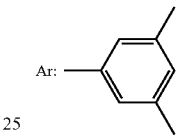

Under nitrogen gas, a mixture of RuCl[(S)-xylbinap][(S)-daipen] 1.00 g (0.844 mmol), which has been obtained in Example 1, NaOTf (CF$_3$SO$_3$Na) 159.7 mg (0.928 mmol) and toluene 20 mL was stirred for 5 hours at room temperature. The reaction solution was filtered and the solvent in the filtrate was removed under reduced pressure to obtain almost quantitatively the title compound (1.10 g).

$^{31}$P-NMR (C$_6$D$_6$): δ
52.5 (d, J=37.5 Hz), 58.6 (d, J=37.5 Hz)
$^{19}$F-NMR (C$_6$D$_6$): δ
−59.2 (s)
TOF-mass m/z=1298.24 (theoretical value 1298.37)

Example 29

Preparation of Ru(OAc)[(S)-xylbinap][(S)-daipen]

[Chem. 37]

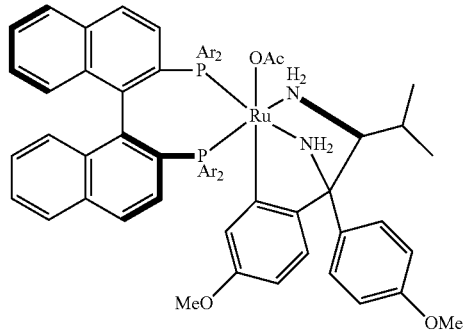

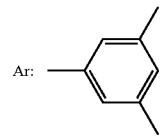

Under nitrogen gas, a mixture of RuCl[(S)-xylbinap][(S)-daipen] 100 mg (0.0844 mmol), which has been obtained in Example 1, NaOAc 13.8 mg (0.169 mmol) and toluene 2 mL was stirred for 10 hours at room temperature. The reaction mixture was filtered and the solvent in the filtrate was removed under reduced pressure to obtain the title compound with yield of 93% (95.2 mg).

$^{31}$P-NMR ($C_6D_6$): δ

51.0 (d, J=37.4 Hz), 60.6 (d, J=38.7 Hz)

ESI: m/z=1209.4337 (theoretical value: 1209.4397 ([M+H]$^+$))

Example 30

Preparation of (S)-1,2,3,4-tetrahydro-1-naphthol

To a 100 mL autoclave with a stirrer, RuCl[(R)-dm-segphos][(S)-daipen] obtained from Example 5 above (3.5 mg, 0.003 mol, 1/1,000 molar fold of 1-tetralone) were added. After purging with nitrogen, 2-propanol (3 mL), 1-tetralone (439 mg, 3 mmol) and 2-propanol solution of t-BuOK (0.1 mol/L, 0.3 mL, 0.03 mmol) were added. Subsequently, purging with hydrogen, the mixture was stirred at 25° C. for 15 hours under hydrogen pressure of 1 MPa. As a result of analysis of the reaction solution by using gas chromatography (Chirasil-DEX CB), it was found that the conversion rate is 99% or more and the optical purity is 96% ex.

Comparative Example 6

Preparation of (S)-1,2,3,4-tetrahydro-1-naphthol

To a 100 mL autoclave with a stirrer, trans-RuCl$_2$[(R)-dm-segphos][(S)-daiPen] (3.6 mg, 0.003 mol, 1/1,000 molar fold of 1-tetralone) was added. After purging with nitrogen, 2-propanol (3 mL), 1-tetralone (439 mg, 3 mmol) and 2-propanol solution of t-BuOK (0.1 mol/L, 0.3 mL, 0.03 mmol) were added. Subsequently, purging with hydrogen, the mixture was stirred at 25° C. for 15 hours under hydrogen pressure of 1 MPa. As a result of analysis of the reaction solution by using gas chromatography (Chirasil-DEX CB), it was found that the conversion rate is 42% and the optical purity is 90% ee.

When Example 30 is compared to Comparative example 5, it was found that the catalytic activity of Comparative example 5 is only 1/2 or less of the catalytic activity of Example 30, and the optical purity of the product obtained is also low in Comparative example 5.

Example 31

Preparation of (S)-1-phenyl-1,2-ethanediol

To a 100 mL autoclave with a stirrer, 2-hydroxyacetophenone (340 mg, 2.5 mmol) and RuCl[(S)-xylbinap][(S)-daipen] obtained from the Example 1 above (1.5 mg, 0.00125 mol, 1/2,000 molar fold of 2-hydroxyacetophenone) were added. After purging with nitrogen, methanol (1.25 mL) and 1,8-diazabicyclo[5.4.0]undeca-7-ene (1.9 mg, 0.0125 mmol) were added. Subsequently, purging with hydrogen, the mixture was stirred at 30° C. for 5 hours under hydrogen pressure of 1 MPa. As a result of analysis of the reaction solution by using gas chromatography (HP-1), the conversion rate was found to be 99% or more. The optical purity was measured by high performance liquid chromatography (CHIRALPAK AS-H, eluent; hexane:2-propanol=92:8), and it was found to be 94% ee.

Example 32

Preparation of (S)-1-phenyl-1,2-ethanediol

Regarding Example 31, except that the use amount of RuCl[(S)-xylbinap][(S)-daipen] was changed (3.0 mg, 0.0025 mol, 1/1,000 molar fold of 2-hydroxyacetophenone) and 2-propanol (2.5 mL) was used instead of methanol, the same procedure as Example 31 was carried out. As a result of analysis of the reaction solution by using gas chromatography (HP-1), the conversion rate was found to be 99% or more. The optical purity was measured by high performance liquid chromatography (CHIRALPAK AS-H, eluent; hexane:2-propanol=92:8), and it was found to be 90% ee.

Comparative Example 7

Preparation of (S)-1-phenyl-1,2-ethanediol

Regarding Example 32, except that trans-RuCl$_2$[(S)-xylbinap][(S)-daipen] was used instead of RuCl[(S)-xylbinap][(S)-daipen], the same procedure as Example 32 was carried out. As a result of analysis of the reaction solution by gas chromatography (HP-1), the conversion rate was 0%, indicating that no title compound was obtained.

When Example 32 is compared to Comparative example 7, it was found that trans-RuCl$_2$[(S)-xylbinap][(S)-daipen] has no catalytic activity.

Example 33

Preparation of (S)-1-(4-methoxyphenyl)-1,2-ethanediol

To a 100 mL autoclave with a stirrer, 2-hydroxy-1-(4-methoxyphenyl)ethanone (415 mg, 2.5 mmol) and RuCl[(S)-xylbinap][(S)-daipen] obtained from the Example 1 above (3.0 mg, 0.0025 mol, 1/1000 molar fold of 2-hydroxy-1-(4-methoxyphenyl)ethanone) were added. After purging with nitrogen, methanol (2.5 mL) and 1,8-diazabicyclo[5.4.0]undeca-7-ene (3.8 mg, 0.025 mmol) were added. Subsequently, after purging with hydrogen, the mixture was stirred at 30° C. for 5 hours under hydrogen pressure of 1 MPa. As a result of analysis of the reaction solution by using gas chromatography (HP-1), the conversion rate was found to be 99% or more. The optical purity was measured by high performance liquid chromatography (CHIRALPAK AS-H, eluent; hexane:ethanol=95:5), and it was found to be 97% ee.

Example 34

Preparation of (S)-1-phenylethanol

Under nitrogen gas, to a mixture of acetophenone (120 mg, 1 mmol), RuCl[(S)-xylbinap][(S)-daipen] obtained from the Example 1 above (6.1 mg, 1/200 molar fold of acetophenone) and 2-propanol 10 mL in a Schlenk tube, 2-propanol solution (0.1 mol/L, 0.25 mL, 0.025 mmol) of t-BuOK was added and stirred at 26° C. for 1 hour. As a result of analysis of the reaction mixture by gas chromatography (Chirasil-DEX CB), it was found that the conversion rate is 96%, and the optical purity is 99% ee.

Comparative Example 8

Regarding Example 34, except that trans-RuCl$_2$-[(S)-xylbinap][(S)-daipen] was used in the same amount instead of RuCl[(S)-xylbinap][(S)-daipen], the same procedure as Example 34 was carried out. As a result of analysis of the reaction mixture by gas chromatography (Chirasil-DEX CB), it was found that the conversion rate is 21%, and the optical purity is 90% ee.

When Example 34 is compared to Comparative example 8, it was found that the catalytic activity of Comparative example 8 is only 1/4 or less of the catalytic activity of Example 34, and the optical purity of the product obtained is also low in Comparative example 8.

The invention claimed is:

1. A ruthenium complex represented by the following Formula (2)

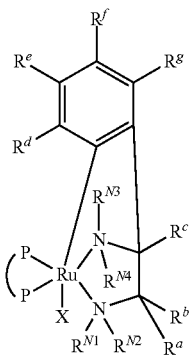

(2)

wherein Ru represents a ruthenium atom; X represents an anionic group; $R^a$, $R^b$, and $R^c$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group or an optionally substituted heterocyclic group, and $R^b$ and $R^c$ may form an alkylene group or an alkylenedioxy group; $R^d$, $R^e$, $R^f$ and $R^g$ each independently represent a hydrogen atom, an alkyl group having 1 to 20 carbon atoms, a halogenated alkyl group having 1 to 5 carbon atoms, a halogen atom, an optionally substituted aryl group, an optionally substituted $C_3$-$C_8$ cycloalkyl group, a tri-substituted silyl group or an alkoxy group having 1 to 20 carbon atoms; $R^{N1}$, $R^{N2}$, $R^{N3}$ and $R^{N4}$ each independently represent a hydrogen atom, or an optionally substituted $C_1$-$C_{20}$ alkyl group, and at least one of $R^{N1}$, $R^{N2}$, $R^{N3}$ and $R^{N4}$ represents a hydrogen atom, and $R^{N1}$ and $R^a$ may form an alkylene group; and P⌒P represents a diphosphine represented by the following Formula (4)

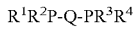

$$R^1R^2P-Q-PR^3R^4 \quad (4)$$

wherein $R^1$, $R^2$, $R^3$ and $R^4$ each independently represent an optionally substituted aryl group, an optionally substituted cycloalkyl group or an optionally substituted alkyl group, and $R^1$ and $R^2$ and/or $R^3$ and $R^4$ may form a ring; and Q represents an optionally substituted divalent arylene group, biphenyldiyl group, binaphthalenediyl group, bipyridinediyl group, para-cyclophanediyl group or ferrocenediyl group.

2. The ruthenium complex according to claim 1, wherein $R^{N1}$, $R^{N2}$, $R^{N3}$ and $R^{N4}$ each represent a hydrogen atom.

3. The ruthenium complex according to claim 1, wherein the ruthenium complex is a ruthenium complex represented by the following Formula (3)

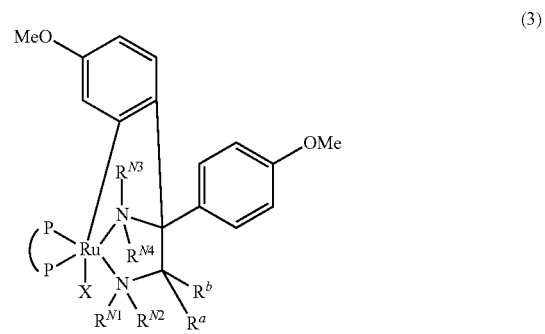

(3)

wherein Ru represents a ruthenium atom; X represents an anionic group; $R^a$ and $R^b$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group or an optionally substituted heterocyclic group; $R^{N1}$, $R^{N2}$, $R^{N3}$ and $R^{N4}$ each independently represent a hydrogen atom, or an optionally substituted $C_1$-$C_{20}$ alkyl group, and at least one of $R^{N1}$, $R^{N2}$, $R^{N3}$ and $R^{N4}$ represents a hydrogen atom, and $R^{N1}$ and $R^a$ may form an alkylene group; P⌒P represents a diphosphine represented by the following Formula (4)

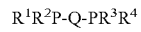

$$R^1R^2P-Q-PR^3R^4 \quad (4)$$

wherein $R^1$, $R^2$, $R^3$ and $R^4$ each independently represent an optionally substituted aryl group, an optionally substituted cycloalkyl group or an optionally substituted alkyl group, and $R^1$ and $R^2$ and/or $R^3$ and $R^4$ may form a ring; and Q represents an optionally substituted divalent arylene group, biphenyldiyl group, binaphthalenediyl group, bipyridinediyl group, para-cyclophanediyl group or ferrocenediyl group.

4. The ruthenium complex according to claim 1, wherein $R^1$, $R^2$, $R^3$ and $R^4$ each independently represent an optionally substituted aryl group.

5. The ruthenium complex according to claim 1, wherein the diphosphine indicated as P⌒P is an optically active diphosphine.

6. The ruthenium complex according to claim 5, wherein the optically active diphosphine indicated as P⌒P is an optically active diphosphine represented by the following Formula (5)

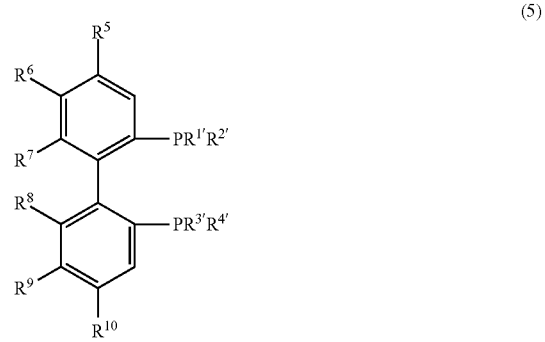

(5)

wherein $R^{1'}$, $R^{2'}$, $R^{3'}$ and $R^{4'}$ each independently represent a phenyl group, a cyclopentyl group or a cyclohexyl group which is optionally substituted with a substituent group selected from a group consisting of an alkyl group having 1 to 4 carbon atoms and an alkoxy group having 1 to 4 carbon atoms; $R^5$, $R^6$, $R^7$, $R^8$, $R^9$ and $R^{10}$ each independently represent a hydrogen atom, an alkyl group having 1 to 4 carbon atoms, an alkoxy group having 1 to 4 carbon atoms, a halogen atom, a halogenated alkyl group or a dialkylamino group having 1 to 4 carbon atoms, and two of $R^5$, $R^6$ and $R^7$ may form an optionally substituted alkylene group, an optionally substituted alkylenedioxy group or an optionally substituted aromatic ring, two of $R^8$, $R^9$ and $R^{10}$ may form an optionally substituted alkylene group, an optionally substituted alkylenedioxy group or an optionally substituted aromatic ring, and $R^7$ and $R^8$ may form an optionally substituted alkylene group, an optionally substituted alkylenedioxy group or an optionally substituted aromatic ring, with the proviso that any of $R^7$ and $R^8$ is not a hydrogen atom.

7. The ruthenium complex according to claim 6, wherein $R^{1'}$, $R^{2'}$, $R^{3'}$ and $R^{4'}$ in the Formula (5) is a 3,5-xylyl group.

8. A catalyst for asymmetric reduction comprising the ruthenium complex according to claim 5.

9. A method for preparing optically active alcohols, wherein a carbonyl group is asymmetrically hydrogenated by the catalyst according to claim 8 in the presence of a base compound.

10. A method for preparing optically active alcohols, wherein a carbonyl group is subjected to asymmetric hydrogen-transfer reduction using the catalyst according to claim 8 in the presence of a base compound.

11. A method for preparing the ruthenium complex represented by the following Formula (2),

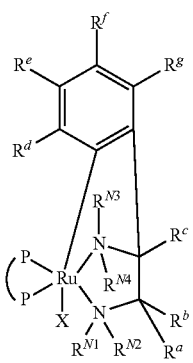

(2)

wherein Ru represents a ruthenium atom; X represents an anionic group; $R^a$, $R^b$, and $R^c$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group or an optionally substituted heterocyclic group, and $R^b$ and $R^c$ may form an alkylene group or an alkylenedioxy group; $R^d$, $R^e$, $R^f$ and $R^g$ each independently represent a hydrogen atom, an alkyl group having 1 to 20 carbon atoms, a halogenated alkyl group having 1 to 5 carbon atoms, a halogen atom, an optionally substituted aryl group, an optionally substituted $C_3$-$C_8$ cycloalkyl group, a tri-substituted silyl group or an alkoxy group having 1 to 20 carbon atoms; $R^{N1}$, $R^{N2}$, $R^{N3}$ and $R^{N4}$ each independently represent a hydrogen atom, or an optionally substituted $C_1$-$C_{20}$ alkyl group, and at least one of $R^{N1}$, $R^{N2}$, $R^{N3}$ and $R^{N4}$ represents a hydrogen atom, and $R^{N1}$ and $R^a$ may form an alkylene group; and P⌒P represents a diphosphine represented by the following Formula (4)

$$R^1R^2P\text{-}Q\text{-}PR^3R^4 \quad (4)$$

wherein $R^1$, $R^2$, $R^3$ and $R^4$ each independently represent an optionally substituted aryl group, an optionally substituted cycloalkyl group or an optionally substituted alkyl group, and $R^1$ and $R^2$ and/or $R^3$ and $R^4$ may form a ring; and Q represents an optionally substituted divalent arylene group, biphenyldiyl group, binaphthalenediyl group, bipyridinediyl group, paracyclophanediyl group or ferrocenediyl group, wherein the ruthenium compound represented by the following Formula (A)

wherein Ru represents a ruthenium atom; X represents a halogen atom; L represents an arene; and P⌒P represents a diphosphine which is the same as that described above, is reacted with the compound having the following Formula (8)

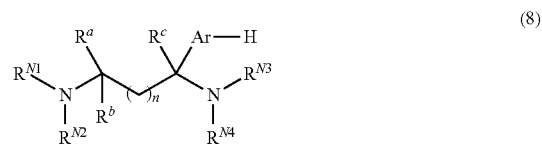

wherein $R^a$, $R^b$, $R^c$, $R^{N1}$, $R^{N2}$, $R^{N3}$, and $R^{N4}$ are the same as those described above; and n represents; and Ar represents a 1,2-phenylene group having substituent groups of $R^d$, $R^e$, $R^f$ and $R^g$, wherein $R^d$, $R^e$, $R^f$ and $R^g$ are the same as those described above.

12. A method for preparing the ruthenium complex represented by the following Formula (2),

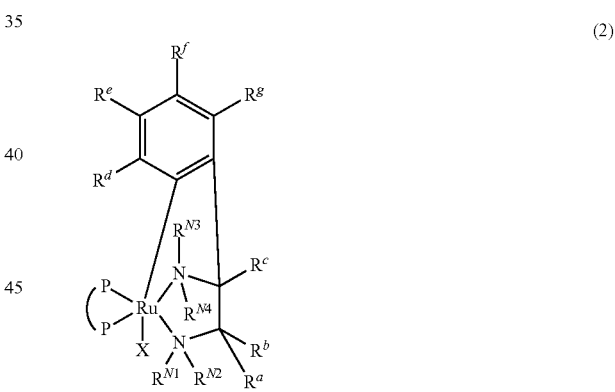

(2)

wherein Ru represents a ruthenium atom; X represents an anionic group; $R^a$, $R^b$, and $R^c$ each independently represent a hydrogen atom, an optionally substituted $C_1$-$C_{20}$ alkyl group, an optionally substituted $C_2$-$C_{20}$ alkenyl group, an optionally substituted $C_3$-$C_8$ cycloalkyl group, an optionally substituted $C_7$-$C_{20}$ aralkyl group, an optionally substituted aryl group or an optionally substituted heterocyclic group, and $R^b$ and $R^c$ may form an alkylene group or an alkylenedioxy group; $R^d$, $R^e$, $R^f$ and $R^g$ each independently represent a hydrogen atom, an alkyl group having 1 to 20 carbon atoms, a halogenated alkyl group having 1 to 5 carbon atoms, a halogen atom, an optionally substituted aryl group, an optionally substituted $C_3$-$C_8$ cycloalkyl group, a tri-substituted silyl group or an alkoxy group having 1 to 20 carbon atoms; $R^{N1}$, $R^{N2}$, $R^{N3}$ and $R^{N4}$ each independently represent a hydrogen atom, or an optionally substituted $C_1$-$C_{20}$ alkyl group, and at least one of $R^{N1}$, $R^{N2}$, $R^{N3}$ and $R^{N4}$ represents a hydrogen atom, and $R^{N1}$ and $R^a$ may form an alkylene group; and P⌒P represents a diphosphine represented by the following Formula (4)

$$R^1R^2P\text{-}Q\text{-}PR^3R^4 \quad (4)$$

wherein $R^1$, $R^2$, $R^3$ and $R^4$ each independently represent an optionally substituted aryl group, an optionally substituted cycloalkyl group or an optionally substituted alkyl group, and $R^1$ and $R^2$ and/or $R^3$ and $R^4$ may form a ring; and Q represents an optionally substituted divalent arylene group, biphenyldiyl group, binaphthalenediyl group, bipyridinediyl group, paracyclophanediyl group or ferrocenediyl group,
wherein the ruthenium compound represented by the following Formula (B)

$$[RuX_2(L)]_m \quad (B)$$

wherein Ru represents a ruthenium atom; X represents a halogen atom; L represents an arene; and m represents 2 is reacted with a diphosphine represented as P⌒P which is the same as that described above, and then with the compound having the following Formula (8)

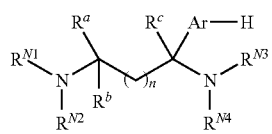

(8)

wherein $R^a$, $R^b$, $R^c$, $R^{N1}$, $R^{N2}$, $R^{N3}$ and $R^{N4}$ are the same as those described above; and n represents 0; and Ar represents a 1,2-phenylene group having substituent groups of $R^d$, $R^e$, $R^f$ and $R^g$, wherein $R^d$, $R^e$, $R^f$ and $R^g$ are the same as those described above.

13. The method for preparing the ruthenium complex according to claim 11, where the reaction is carried out in the presence of solvent, wherein the solvent used is an alcohol solvent.

14. The method for preparing the ruthenium complex according to claim 11, additionally wherein a base is added.

15. The method for preparing the ruthenium complex according to claim 11, wherein the diphosphine indicated as P⌒P is an optically active diphosphine.

16. The method for preparing the ruthenium complex according to claim 11, wherein the diphosphine indicated as P⌒P is an optically active diphosphine represented by the following Formula (5)

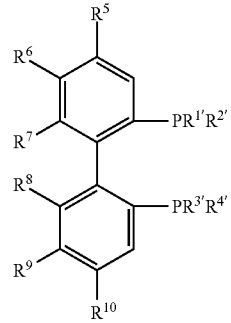

(5)

wherein $R^{1'}$, $R^{2'}$, $R^{3'}$ and $R^{4'}$ each independently represent a phenyl group, a cyclopentyl group or a cyclohexyl group which is optionally substituted with a substituent group selected from a group consisting of an alkyl group having 1 to 4 carbon atoms and an alkoxy group having 1 to 4 carbon atoms; $R^5$, $R^6$, $R^7$, $R^8$, $R^9$ and $R^{10}$ each independently represent a hydrogen atom, an alkyl group having 1 to 4 carbon atoms, an alkoxy group having 1 to 4 carbon atoms, a halogen atom, a halogenated alkyl group or an dialkylamino group having 1 to 4 carbon atoms, and two of $R^5$, $R^6$ and $R^7$ may form an optionally substituted alkylene group, an optionally substituted alkylenedioxy group or an optionally substituted aromatic ring, and two of $R^8$, $R^9$ and $R^{10}$ may form an optionally substituted alkylene group, an optionally substituted alkylenedioxy group or an optionally substituted aromatic ring; and $R^7$ and $R^8$ may form an optionally substituted alkylene group, an optionally substituted alkylenedioxy group or an optionally substituted aromatic ring, with the proviso that $R^7$ and $R^8$ are not a hydrogen atom.

17. The method for preparing the ruthenium complex according to claim 16, wherein $R^{1'}$, $R^{2'}$, $R^{3'}$ and $R^{4'}$ in the Formula (5) is a 3,5-xylyl group.

18. A catalyst for asymmetric reduction comprising the ruthenium complex according to claim 6.

19. A catalyst for asymmetric reduction comprising the ruthenium complex according to claim 7.

* * * * *